US006495591B1

(12) United States Patent
Chamberland et al.

(10) Patent No.: US 6,495,591 B1
(45) Date of Patent: Dec. 17, 2002

(54) FUNGAL EFFLUX PUMP INHIBITORS

(75) Inventors: Suzanne Chamberland, Los Gatos, CA (US); May Lee, Los Altos, CA (US); Olga Lomovskaya, Mill Valley, CA (US)

(73) Assignee: Essential Therapeutics, Inc., Mountain View, CA (US)

( * ) Notice: Subject to any disclaimer, the term of this patent is extended or adjusted under 35 U.S.C. 154(b) by 0 days.

(21) Appl. No.: 09/164,609

(22) Filed: Oct. 1, 1998

Related U.S. Application Data

(60) Provisional application No. 60/061,322, filed on Oct. 2, 1997.

(51) Int. Cl.$^7$ .............................................. A61K 31/335

(52) U.S. Cl. ........................ 514/450; 514/30; 514/63; 514/409; 514/278; 514/432; 514/444

(58) Field of Search ........................ 514/450, 30, 63, 514/409, 278, 432, 444

(56) References Cited

U.S. PATENT DOCUMENTS

| | | | |
|---|---|---|---|
| 3,950,360 A | 4/1976 | Aoki et al. ............ 260/343.2 R |
| 3,992,551 A | 11/1976 | Acki et al. .................... 424/283 |
| 4,093,629 A | 6/1978 | Fisher .................... 260/326.34 |
| 4,134,973 A | 1/1979 | Fisher et al. ................. 424/180 |
| 4,144,352 A | 3/1979 | Putter .......................... 424/279 |
| 4,547,520 A | 10/1985 | Ide et al. ..................... 514/450 |
| 4,847,243 A | * 7/1989 | Wallace ........................ 514/30 |
| 4,886,829 A | 12/1989 | Asato et al. ................. 514/450 |
| 4,916,154 A | 4/1990 | Asato et al. ................. 514/450 |
| 4,988,824 A | 1/1991 | Maulding et al. ............ 549/264 |
| 5,001,145 A | * 3/1991 | Ramsay et al. .............. 514/450 |
| 5,030,650 A | 7/1991 | Buckwalter et al. ......... 514/450 |
| 5,106,994 A | 4/1992 | Carter et al. ................ 549/264 |
| 5,149,832 A | 9/1992 | Asato ........................... 549/264 |
| 5,169,956 A | 12/1992 | Carter et al. ................ 549/264 |
| 5,474,997 A | * 12/1995 | Gray et al. .................. 514/252 |

FOREIGN PATENT DOCUMENTS

| | | |
|---|---|---|
| AU | 23602/35 | 7/1935 |
| AU | 17168/83 | 1/1984 |
| DE | 39 16931 A1 | 12/1990 |
| EP | 0 204 421 A1 | 12/1986 |
| EP | 0 205 251 A1 | 12/1986 |
| EP | 0 237 341 | 9/1987 |
| EP | 0 242 052 A2 | 10/1987 |
| EP | 0 254 583 A2 | 1/1988 |
| EP | 0 280 928 B1 | 9/1988 |
| EP | 0 298 423 A2 | 1/1989 |
| EP | 0 300 674 A2 | 1/1989 |
| EP | 0 308 145 A2 | 3/1989 |
| EP | 0 325 462 A2 | 7/1989 |
| EP | 0 334 484 A2 | 9/1989 |
| EP | 0 369 502 A2 | 5/1990 |
| EP | 0 410 615 A1 | 1/1991 |
| EP | 0 444 964 B1 | 9/1991 |
| EP | 0 475 518 A1 | 3/1992 |
| EP | 0 478 064 A2 | 4/1992 |
| EP | 0 511 881 A1 | 11/1992 |
| GB | 2 166 436 A | 5/1986 |
| GB | 2167751 | 6/1986 |
| GB | 2 170 499 B | 8/1986 |
| GB | 2 187 742 A | 9/1987 |
| JP | 63-264484 | 1/1988 |
| JP | 63-227590 | 9/1988 |
| WO | 95/20980 | 8/1995 |
| WO | 96/01127 | 1/1996 |
| WO | 96/21427 | 7/1996 |
| WO | 96/33285 | 10/1996 |
| WO | 97/15269 | 5/1997 |
| WO | 9848813 | * 11/1998 |

OTHER PUBLICATIONS

Albertson et al., "Multiple efflux mechanisms are involved in *Candida albicans* fluconazole resistance," *Antimicrob. Agents Chemother.* 40:2835–2841 (1996).
Baker et al., "A novel series of milbemycin antibiotics from streptomyces strain E225," *Journal of Antibiotics* XLIII(9):1069–1076 (1990).
Baker et al., "Further novel milbemycin antibiotics from streptomyces sp. E225 fermentation, isolation and structure elucidation," *Journal of Antibiotics* 49:272–280 (1996).
Borst et al., "New mechanisms of drug resistance in parasitic protozoa," *Annu. Rev. Microbiol.* 49:427–60 (1995).
Bossche et al., "Characterization of an azole resistant *Candida albicans* isolate," *Antimicrob. Agents and Chemother.* 36:2602–2610 (1992).
Bossche et al., "Molecular mechanisms of drug resistance in fungi," *Trends Microbiol.* 2:393–400 (1994).
Carter et al., "LL–F28249 antibiotic complex: A new family of antiparasitic macrocyclic lactones," *Journal of Antibiotics* XLI(4):519–529 (1988).
Davies et al., "Avermectins and milbemycins Part I," *Chem. Soc. Rev.* 20:211–269 (1991).
De Waard et al., "An energy–dependent efflux mechanism for fenarimol in a wild type strain and fenarimol–resistant mutants of *Aspergillus nidulans*," *Pesticide Biochem. Physiol.* 13:255–266 (1980).
Fling et al., "Analysis of a *Candida albicans* gene that encodes a novel mechanism for resistance to benomyl and methotrexate," *Mol. Molec. Genet.* 227:318–329 (1991).
Fonzi et al., "Isogenic strain construction and gene mapping in *Candida albicans*," *Genetics* 134:717–728 (1992).

(List continued on next page.)

*Primary Examiner*—Zohreh Fay
*Assistant Examiner*—C. Delacroix-Muirheid
(74) *Attorney, Agent, or Firm*—Bingham McCutchen; Bernard F. Rose

(57) ABSTRACT

The use of compounds of the milbemycin class as inhibitors of efflux pumps in microbes or other cells is described, along with pharmaceutical compositions incorporating a milbemycin. Also described is a method of screening for compounds which inhibit a CDR1, CDR2, BEN, or FLU1 efflux pump or a pump with components having a high level of protein level sequence similarity with the components of those efflux pumps.

12 Claims, 36 Drawing Sheets

OTHER PUBLICATIONS

Gottesman et al., "Biochemistry of multidrug resistance mediated by the multidrug transporter," *Annu. Rev. Biochem.* 62:385–427 (1993).

Haxell et al., "C–13β–acyloxymilbemycins, a new family of macrolides," *Journal of Antibiotics* 45:659–670 (1992).

Higgins, C.F., "ABC transporters: From microorganisms to man," *Annu. Rev. Cell Biol.* 8:67–113 (1992).

Hitchcock, C.A., "Resistance of *Candida albicans* to azole antifungal agents," *Biochem. Soc. Trans.* 21:1039–1047 (1993).

Marichal et al., "Origin of differences in susceptibility of *Candida krusei* to azole antifungal agents," *Mycoses* 38:111–117 (1995).

Mishima et al., "Milbemycins, a new family of macrolide antibiotics structure determination of milbemycins," *Journal of Antibiotics* XXXVI(8):980–990 (1983).

Odds, "Resistance of yeasts to azole–derivative antifungals," *J. Antimicrob. Chemother.* 31:463–471 (1993).

Okazaki et al., "Milbemycins, a new family of macrolide antibiotics: producing organism and its mutants," *J. Antibiotics* 36:438–441 (1983).

Parkinson et al., "Fluconazole resistance due to energy–dependent drug efflux in *Candida glabrata*," *Antimicrob. Agents Chemother.* 39:1696–1699 (1995).

Powderly, "Resistant Candidiasis," *AIDS research and Human Retrovirusses* 10:925–929 (1994).

Prasad et al., "Molecular cloning and characterization of a novel gene from *Candida albicans*, CDR1, conferring multiple resistance to drugs and antifungals," *Curr. Genet.* 27:320–329 (1995).

Ramsey et al., "Novel antiparasitic agents derived by modification of a new natural product series," *Tetrahedron Lett.*, 28:5353–5356 (1987).

Raymond et al., "Functional expression of P–glycoprotein in *Saccharomyces cerevisiae* confers cellular resistance to the immunosupressive and antifungal agent FK520," *Mol. and Cellular Biol.* 14:277–286 (1994).

Rex et al., "Resistance of Candida species to fluconazole," *Antimicrob. Agents and Chemother.* 39:1–8 (1995).

Saag et al., "Azole antifungal agents: emphasis on new triazoles," *Antimicrob. Agents Chemother.* 32:1–8 (1988).

Sanglard et al., "Cloning of *Candida albicans* genes conferring resistance to azole antifungal agents: characterization of CDR2, a new multidrug AB transporter gene," *Microbiology* 143:405–416 (1997).

Sanglard et al., "Mechanisms of resistance to azole antifungal agents in *Candida albicans* isolates from AIDS patients involve specific multidrug transporters," *Antimicrob. Agents Chemother.* 39:2378–2386 (1995).

Sanglard et al., "Susceptibilities of *Candida albicans* multidrug transporter mutants to various antifungal agents and other metabolic inhibitors," *Antimicrob. Agents and Chemother.* 40:2300–2305 (1996).

Shepherd et al., "*Candida alibicans*: Biology, genetics, and pathogenicity," *Ann. Rev. Microbiol.* 39:579–614 (1985).

Takiguchi et al., "Milbemycins, a new family of macrolide antibiotics: Fermentation, isolation and physico–chemical properties," *Journal of Antibiotics* 33(10):1120–1127 (1980).

Tsuruo et al., "Overcoming of vincristine resistance in P388 leukemia in vivo and in vitro through enhanced cytotoxicity of vincristine and vinblastine by verapamil," *Cancer Research* 41:1967–1972 (1981).

* cited by examiner

| $R_1$ | $R_2$ | $R_3$ | $R_4$ |
|---|---|---|---|
| OH | H | H | $CH_3$ |
| OH | H | H | $CH_2CH_3$ |
| =O | $CH_3$ | OH | $CH_2CH_3$ |
| OH | $CH_3$ | OH | $CH_2CH_3$ |

R[1] = CH₃, CH₃CH₂ or (CH₃)₂CH

R[2] = hydrogen or CH₃

FIGURE 6A

α-Milbemycins

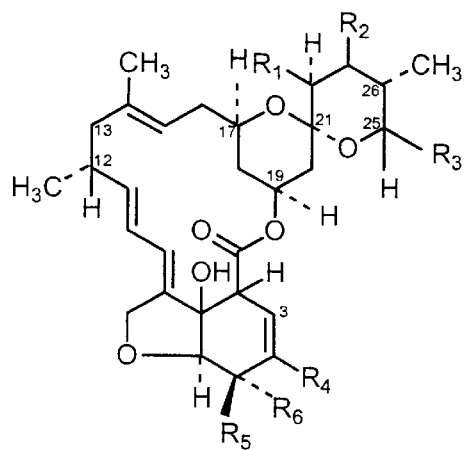

|  | R₁ | R₂ | R₃ | R₄ | R₅ | R₆ |
|---|---|---|---|---|---|---|
| α₁ | H | H | CH₃ | CH₃ | OH | H |
| α₂ | H | H | CH₃ | CH₃ | OCH₃ | H |
| α₃ | H | H | C₂H₅ | CH₃ | OH | H |
| α₄ | H | H | C₂H₅ | CH₃ | OCH₃ | H |
| α₅ | OH | OCOCH(CH₃)C₄H₉ | CH₃ | CH₃ | OH | H |
| α₆ | OH | OCOCH(CH₃)C₄H₉ | CH₃ | CH₃ | OCH₃ | H |
| α₇ | OH | OCOCH(CH₃)C₄H₉ | C₂H₅ | CH₃ | OH | H |
| α₈ | OH | OCOCH(CH₃)C₄H₉ | C₂H₅ | CH₃ | OCH₃ | H |
| α₉ | H | H | CH₃ | CH₂OCO-pyrrole | OH | H |
| α₁₀ | H | H | C₂H₅ | CH₂OCO-pyrrole | OH | H |
| D | H | H | H | CH₃ | OH | H |
| F | H | H | CH(CH₃)₂ | CH₂OCO-pyrrole | OH | H |
| G | H | H | CH(CH₃)₂ | CH₃ | OCH₃ | |
|  | H | H | CH₃ | CH₃ | =O | |
| K | H | H | C₂H₅ | CH₃ | =O | |

β-Milbemycins

FIGURE 6A-2

|   | $R_1$ | $R_2$ | $R_3$ | $R_4$ |
|---|---|---|---|---|
| $\beta_1$ | $CH_3OH$ | $CH_3$ | $OCH_3$ | H |
| $\beta_2$ | $CH_3OH$ | $C_2H_5$ | $OCH_3$ | H |
| E | $CH_3OH$ | $CH(CH_3)_2$ | $OCH_3$ | H |
| H | $CH_3$ | $CH(CH_3)_2$ | = O | |

FIGURE 6B
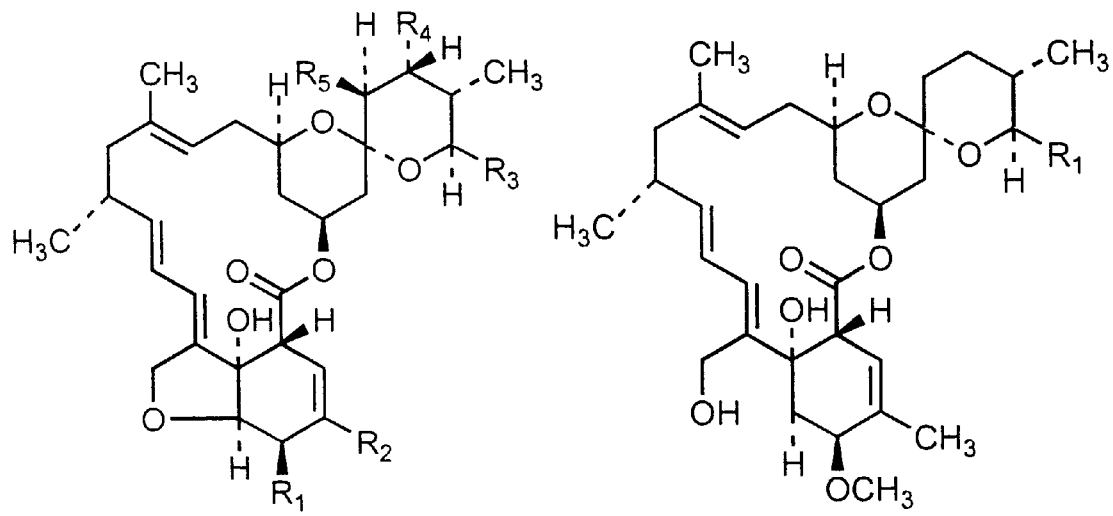
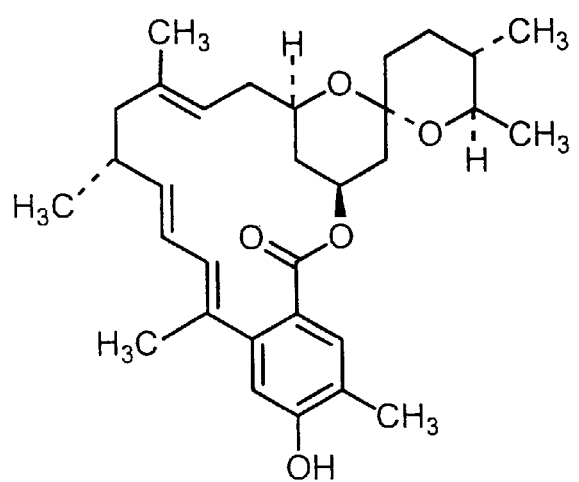

FIGURE 6B-1

| (I) Milbemycins (B-41) | $R_1$ | $R_2$ | $R_3$ | $R_4$ | $R_5$ |
|---|---|---|---|---|---|
| $\alpha_1$ (A$_3$) | OH | CH$_3$ | CH$_3$ | H | H |
| $\alpha_2$ (B$_2$) | OCH$_3$ | CH$_3$ | CH$_3$ | H | H |
| $\alpha_3$ (A$_4$) | OH | CH$_3$ | C$_2$H$_5$ | H | H |
| $\alpha_4$ (B$_3$) | OCH$_3$ | CH$_3$ | C$_2$H$_5$ | H | H |
| $\alpha_5$ (A$_2$) | OH | CH$_3$ | CH$_3$ | OCOCH(CH$_3$)(CH$_2$)$_3$CH$_3$ | OH |
| $\alpha_6$ (B$_1$) | OCH$_3$ | CH$_3$ | CH$_3$ | OCOCH(CH$_3$)(CH$_2$)$_3$CH$_3$ | OH |
| $\alpha_7$ | OH | CH$_3$ | C$_2$H$_5$ | OCOCH(CH$_3$)(CH$_2$)$_3$CH$_3$ | OH |
| $\alpha_8$ | OCH$_3$ | CH$_3$ | C$_2$H$_5$ | OCOCH(CH$_3$)(CH$_2$)$_3$CH$_3$ | OH |
| $\alpha_9$ (C$_1$) | OH | H$_3$CH$_2$OC(O)–(2-pyrrolyl) | CH$_3$ | H | H |
| $\alpha_{10}$ (C$_2$) | OH | H$_3$CH$_2$OC(O)–(2-pyrrolyl) | C$_2$H$_5$ | H | H |

|  | $R^1$ | $R^2$ | $R^3$ |
|---|---|---|---|
| $A_3$ | H | $CH_3$ | $CH_3$ |
| $A_2$ | H | $CH_3$ | $C_2H_5$ |
| $B_4$ | $CH_3$ | $CH_3$ | $CH_3$ |
| $B_3$ | $CH_3$ | $CH_3$ | $C_2H_5$ |
| $C_2$ | H | —$H_2COC(=O)$-(pyrrole) | $CH_3$ |
| $C_1$ | H | —$H_2CH_2OC(=O)$-(pyrrole) | $C_2H_5$ |

|   | $R_1$ | $R_2$ | $R_3$ |
|---|---|---|---|
| 1 | Pentanoyl-oxy | Methyl | methoxy |
| 2 | Hydrogen | methyl | methoxy |
| 3 | Hydrogen | ethyl | methoxy |
| 4 | Heptanoyl-oxy | methyl | hydroxy |
| 5 | Heptanoyl-oxy | methyl | methoxy |

N787-182 complex Milbemycins

| R | R₁ | R₂ | R₃ |
|---|---|---|---|
| H | OCOCHMe₂ | H | H |
| Me | OCOCHMe₂ | H | H |
| Me | OH | OH | H |
| H | OCOCHMe₂ | OH | H |
| Me | OCOCHMe₂ | OH | H |
| H | H | OH | OCOCHMe₂ |
| Me | H | OH | OCOCHMe₂ |
| H | OH | OH | OCOCHMe₂ |
| Me | OH | OH | OCOCHMe₂ |
| H | OCOCHMe₂ | OH | OCOCHMe₂ |
| Me | OCOCHMe₂ | OH | OCOCHMe₂ |
| Me | OCOCHMeEt | OH | OCOCHMe₂ |

FIGURE 9A
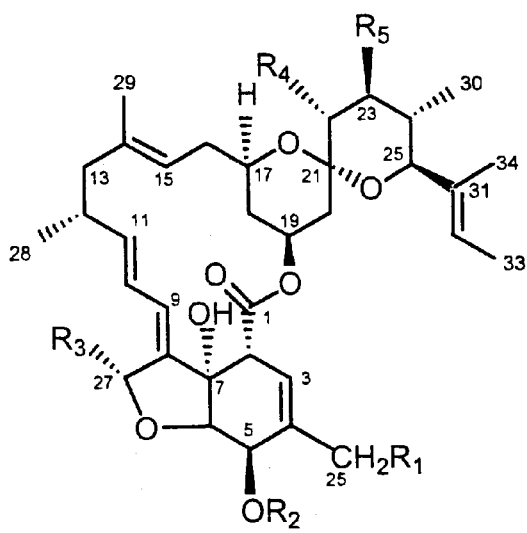
| R₁ | R₂ | R₂ | R₃ | R₅ |
|---|---|---|---|---|
| 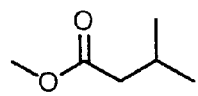 | H | H | OH | H |
| H | H | H | OH | 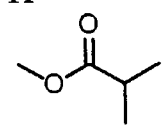 |
| 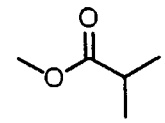 | H | H | OH | H |
| H | Me | OMe | OH | H |
| 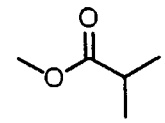 | H | H | OH | H |
| H | H | H | H | H |
| H | Me | H | OH | H |
| OCOC(Me)=CHMe | Me | H | OH | H |
| H | H | H | OH | H |

| R₁ | R₂ | R₃ | R₄ |
|---|---|---|---|
| H, OCH₃ | OH | OH | OH |
| O | H | OH | H |
| H, OCH₃ | H | OH | OH |
| H, OH | H | =O | H |

FIGURE 9C
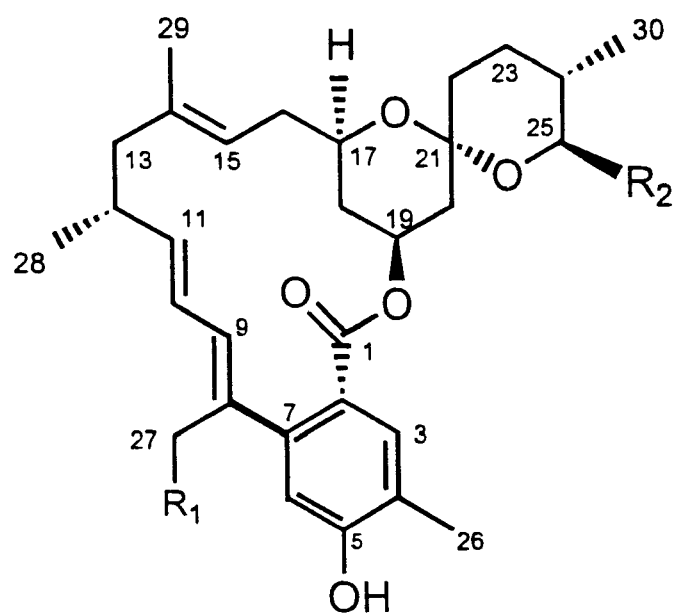
|  | $R_1$ | $R_2$ |
|---|---|---|
| Milbemycin β$_3$ | H | Me |
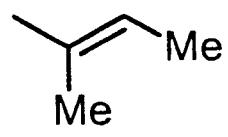

FIGURE 10A
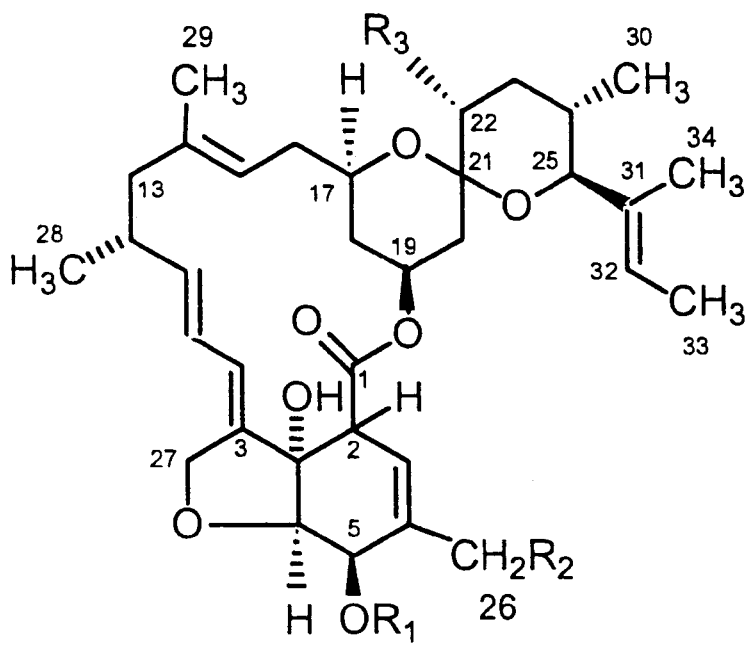
| R₁ | R₂ | R₃ |
|---|---|---|
| H | H | H |
| CH₃ | H | OH |
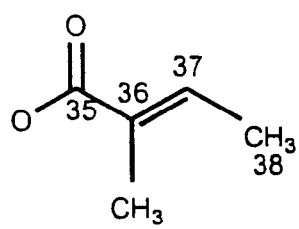
| | | |
|---|---|---|
| CH₃ | | OH |
| H | H | OH |

FIGURE 10B
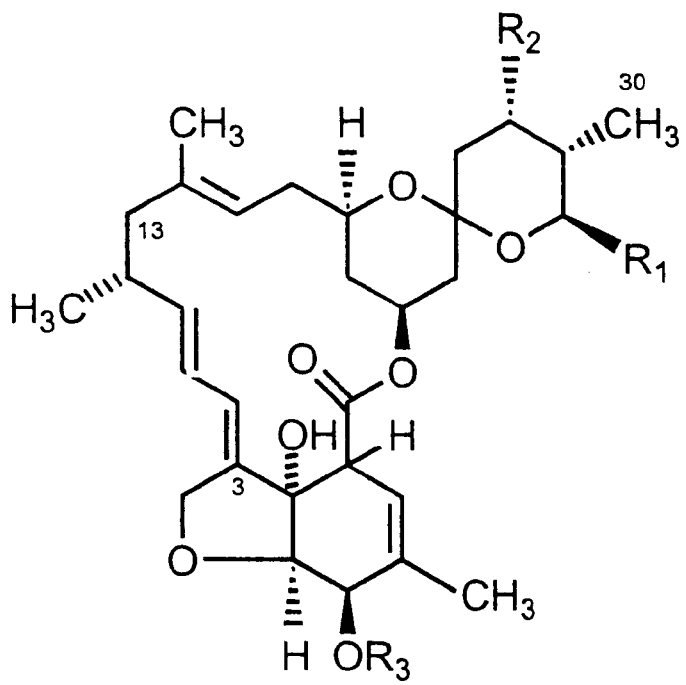
| $R_1$ | $R_2$ | $R_3$ |
|---|---|---|
| $CH(CH_3)_2$ | H | H |
| 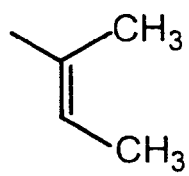 | OH | H |
| 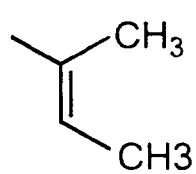 | $OCOCH_3$ | $COCH_3$ |

FIGURE 11A

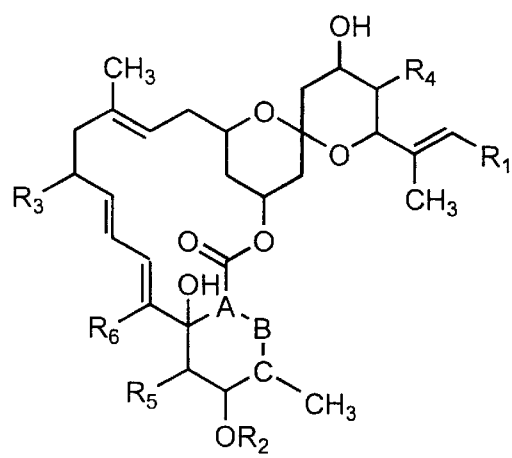

| $R_1$ | $R_2$ | $R_3$ | $R_4$ | $R_5$ | $R_6$ | $R_5 + R_6$ | A - B | B - C |
|---|---|---|---|---|---|---|---|---|
| CH(CH$_3$)$_2$ | H | CH$_3$ | CH$_3$ | | | -O-CH$_2$- | CH-CH | CH=C |
| CH$_3$ | H | CH$_3$ | CH$_3$ | | | -O-CH$_2$- | CH-CH | CH=C |
| CH$_3$ | CH$_3$ | CH$_3$ | CH$_3$ | | | -O-CH$_2$- | CH-CH | CH=C |
| CH$_3$ | CH$_3$ | CH$_3$ | CH$_3$ | OH | CH$_2$OH | | CH-CH | CH=C |
| CH(CH$_3$)$_2$ | H | H | CH$_3$ | | | -O-CH$_2$- | CH-CH | CH=C |
| CH$_2$CH$_3$ | H | CH$_3$ | CH$_3$ | | | -O-CH$_2$- | CH-CH | CH=C |
| CH(CH$_3$)$_2$ | H | CH$_3$ | CH$_3$ | | | -O-CH$_2$- | C=CH | CH-CH |
| CH(CH$_3$)$_2$ | H | CH$_3$ | CH$_2$CH$_3$ | | | -O-CH$_2$- | CH-CH | CH=C |
| CH(CH$_3$)$_2$ | H | CH$_2$CH$_3$ | CH$_3$ | | | -O-CH$_2$- | CH-CH | CH=C |
| CH$_3$ | CH$_3$ | CH$_3$ | CH$_3$ | H | CH$_3$ | | CH-CH | CH=C |
| CH(CH$_3$)$_2$ | CH$_3$ | CH$_3$ | CH$_3$ | | | -O-CH$_2$- | CH-CH | CH=C |
| CH(CH$_3$)$_2$ | CH$_3$ | CH$_3$ | CH$_3$ | H | CH$_3$ | | CH-CH | CH=C |

FIGURE 11B
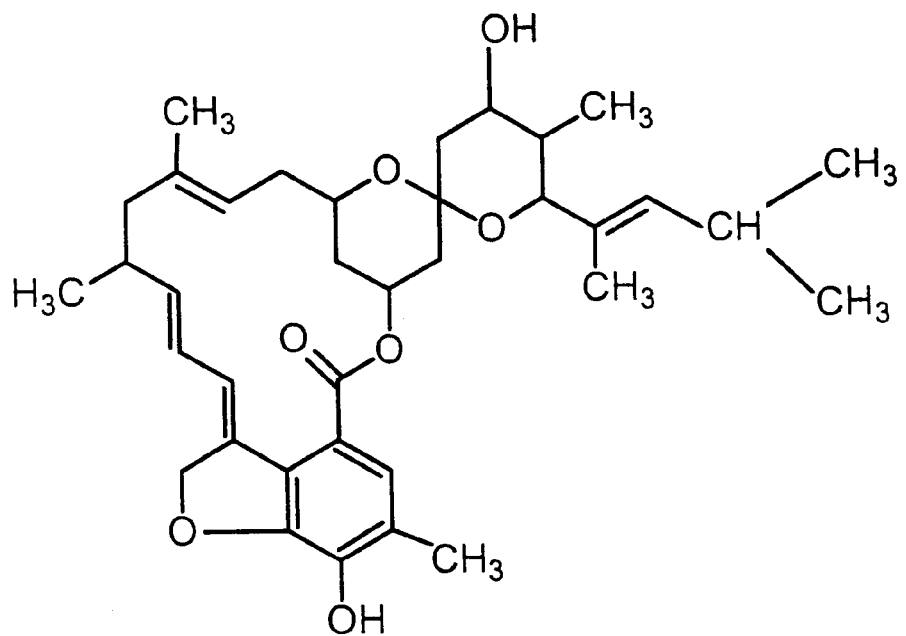
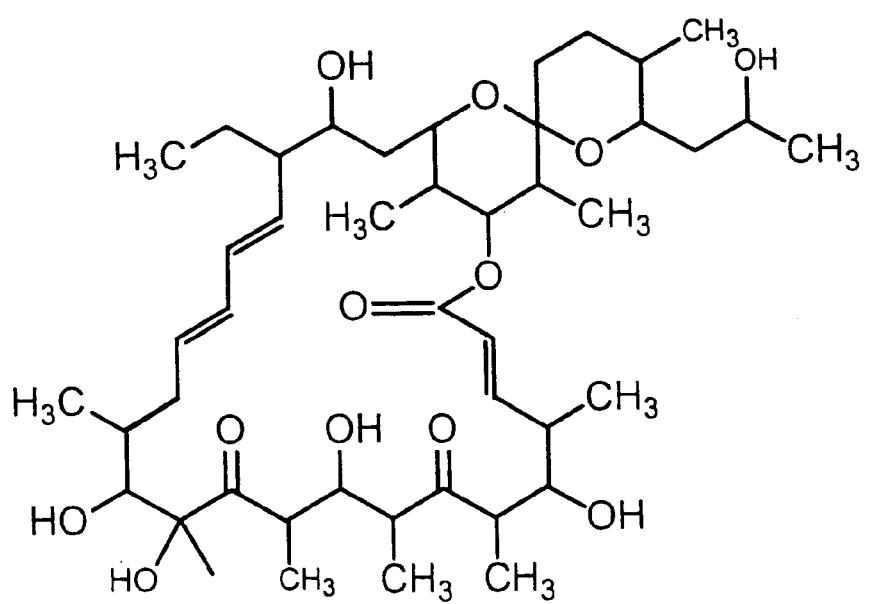

FIGURE 12A
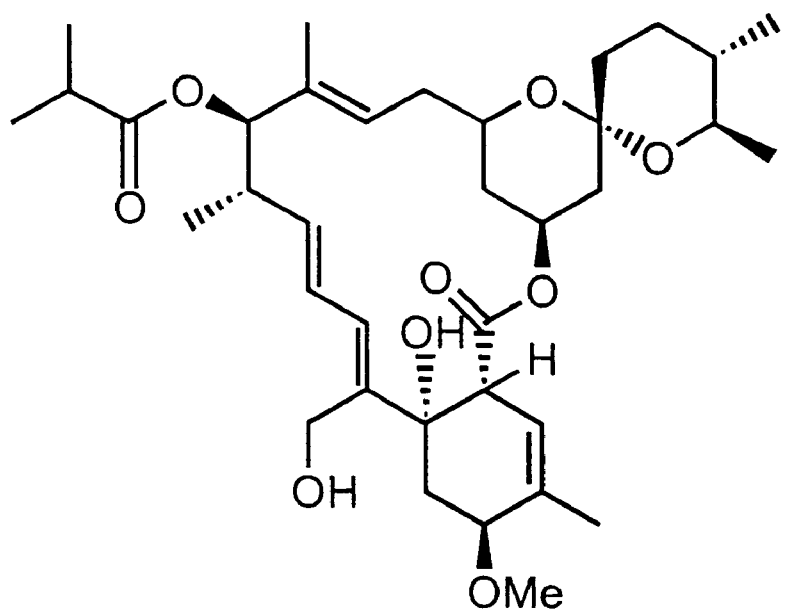
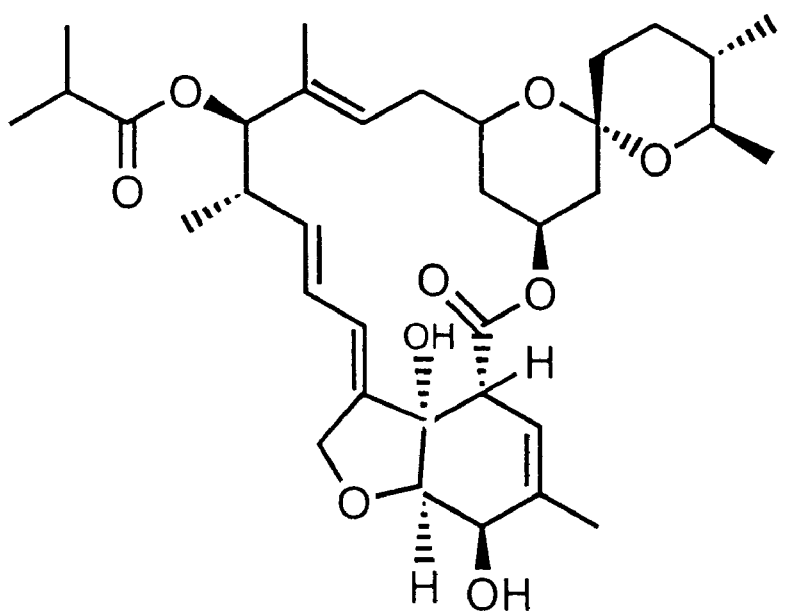

FIGURE 12B
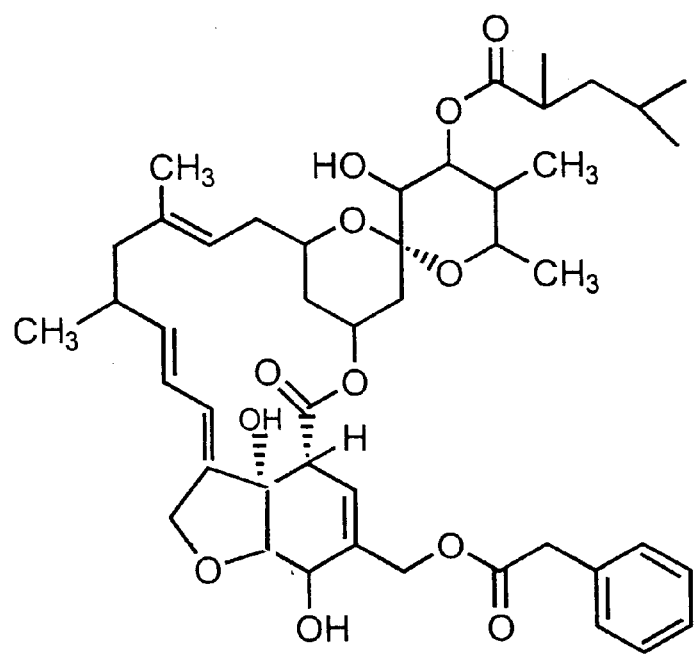
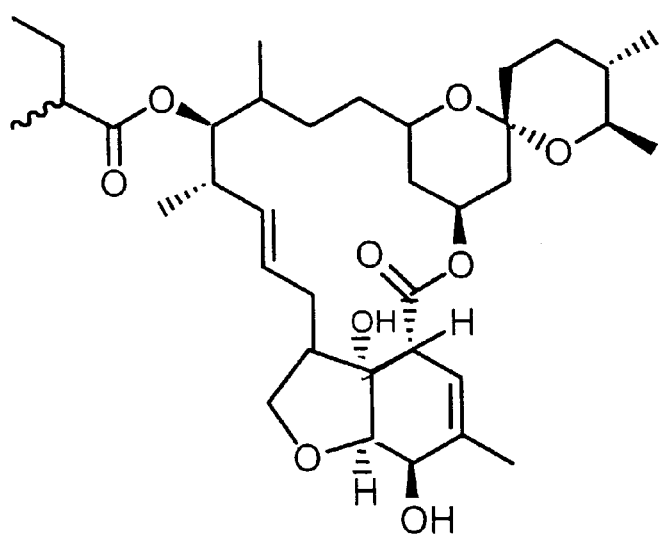

FIGURE 13
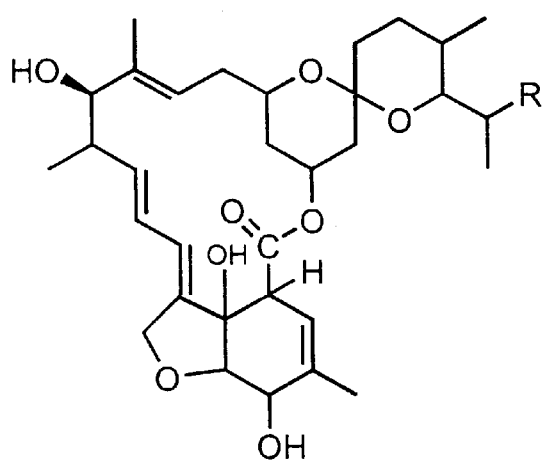
R = CH₃ or CH₃CH₂
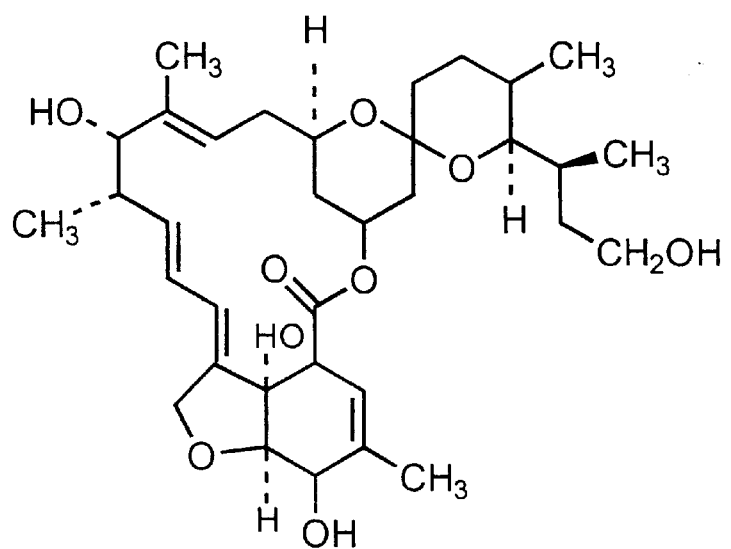
FIGURE 14

FIGURE 16A

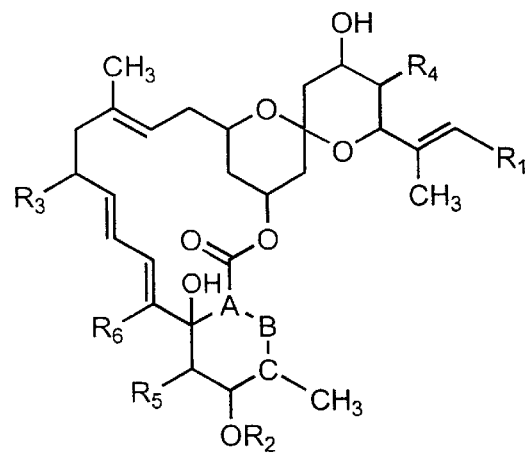

| R₁ | R₂ | R₃ | R₄ | R₅ | R₆ | R₅+R₆ | | B-C |
|---|---|---|---|---|---|---|---|---|
| —CH(CH₃)CH₂OH | H | CH₃ | CH₃ | | | —O—CH₂— | CH-CH | CH=C |
| —O—CH₂ | H | CH₃ | CH₃ | | | —O—CH₂— | CH-CH | CH=C |
| —CH₂OH | CH₃ | CH₃ | CH₃ | | | —O—CH₂— | CH-CH | CH=C |
| —CH₂CH2OH | CH₃ | CH₃ | CH₃ | OH | CH₂OH | | CH-CH | CH=C |
| —CH(CH₃)CH₂OH | H | H | CH₃ | | | —O—CH₂— | CH-CH | CH=C |
| —CH₂CH2OH | H | CH₃ | CH₃ | | | —O—CH₂— | CH-CH | CH=C |
| —CH(CH₃)CH₂OH | H | CH₃ | CH₃ | | | —O—CH₂— | CH-CH | CH-CH |
| —CH(CH₃)CH₂OH | H | CH₃ | CH₂CH₃ | | | —O—CH₂— | CH-CH | CH=C |
| —CH(CH₃)CH₂OH | H | CH₂CH₃ | CH₃ | | | —O—CH₂— | CH-CH | CH=C |
| —CH₂OH | CH₃ | CH₃ | CH₃ | H | CH₃ | | CH-CH | CH=C |
| —CH(CH₃)CH₂OH | CH₃ | CH₃ | CH₃ | | | —O—CH₂— | CH-CH | CH=C |
| —CH(CH₃)CH₂OH | CH₃ | CH₃ | CH₃ | H | CH₃ | | CH-CH | CH=C |

| R | R¹ | R² | R³ |
|---|---|---|---|
| CH₃ | OH | OH | H |
| H | OH | OH | OCOCH(CH₃)₂ |
| CH₃ | OH | OH | OCOCH(CH₃)₂ |
| H | OCOCH(CH₃)₂ | OH | H |
| CH₃ | OCOCH(CH₃)₂ | OH | H |
| H | OCOCH(CH₃)₂ | OH | OCOCH(CH₃)₂ |
| CH₃ | OCOCH(CH₃)₂ | OH | OCOCH(CH₃)₂ |
| H | H | OH | OCOCH(CH₃)₂ |
| H | OCOCH(CH₃)₂ | H | H |
| CH₃ | OCOCH(CH₃)CH₂CH₃ | OH | OCOCH(CH₃)₂ |
| CH₃ | H | OH | OCOCH(CH₃)₂ |
| CH₃ | OCOCH(CH₃)₂ | H | H |
| H | OH | OH | H |
| H | OH | H | H |
| CH₃ | OH | H | H |

$R^3$ and one of $R^4$ and $R^5$ is hydroxy, the other of $R^4$ and $R^5$ is hydrogen.

FIGURE 19

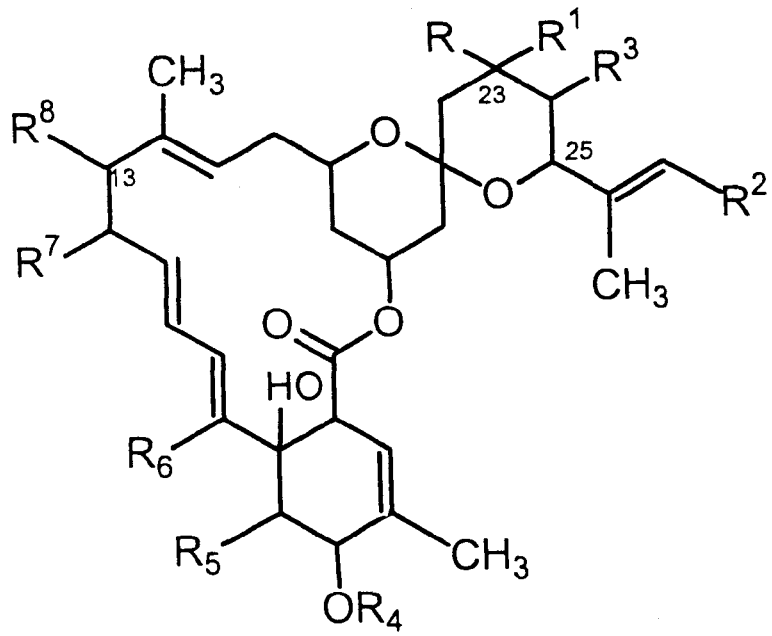

R is hydrogen, $R^1$ = OH; or, R, $R^1$ is =O $R^2$ is (3C – 8C)alkyl, alkenyl, alkynyl optionally containing a oxygen or sulfur in the chain; (3C – 6C)cycloakyl or cycloalkenyl; 3 – 6 member oxygen or sulfur-containing heterocyclic optionally substituted with one or more (1C – 4C)alkyl groups or halogen atoms;

$R^3$ is methyl or ethyl;

$R^4$ is hydrogen or methyl;

Either $R^5$ is hydrogen or hydroxy and $R^6$ is methyl or hydroxymethyl, or $R^5$ and $R^6$, taken together, are –O-CH$_2$-;

$R^7$ is hydrogen, methyl or ethyl; and $R^8$ is hydrogen or halogen.

FIGURE 21
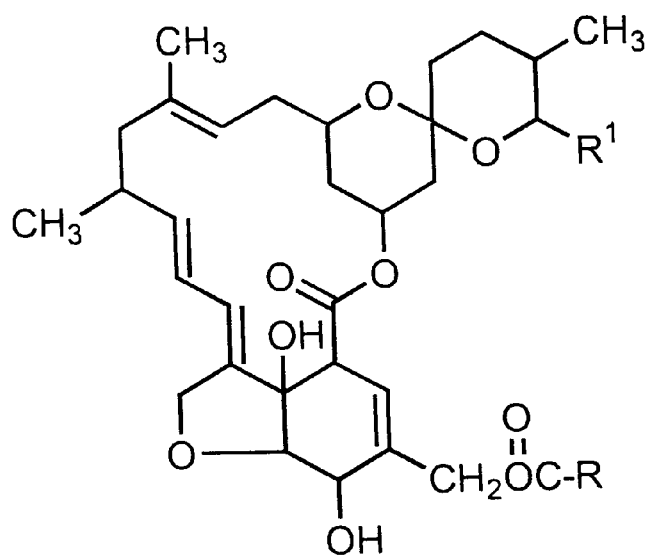
R =
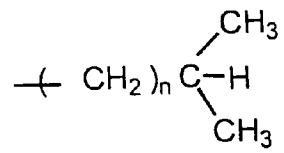
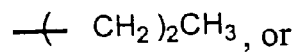
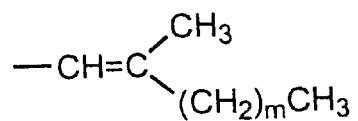
$R^1 = CH_3$ or $CH_3CH_2$;
n = 0, 1 or 2
m = 0 or 1

(I)

R¹ = hydrogen or CH₃;

R² = hydrogen or E-2-methyl-2-butenoxloxy;

R³ = hydrogen or OH.

FIGURE 22B
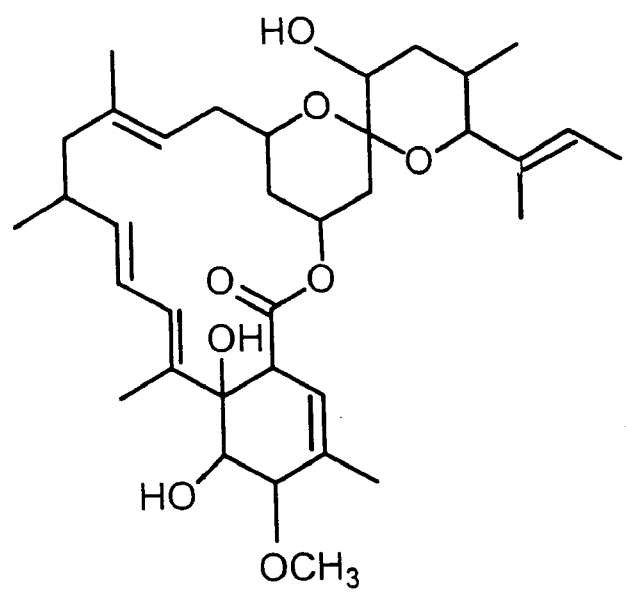
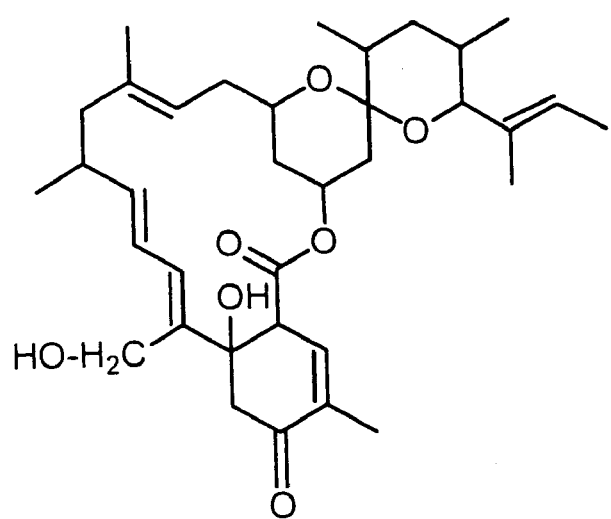

FIGURE 23A
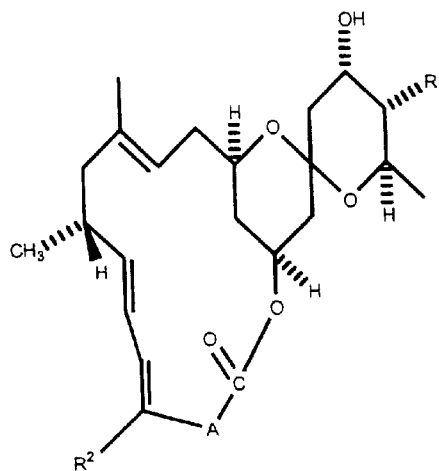
$R^1 = CH_3$;
$R^2 = CH_3$;
$R^3 = CH_3$, $CH_3CH_2$ or $(CH_3)_2CH$
A =
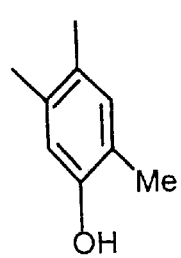 or 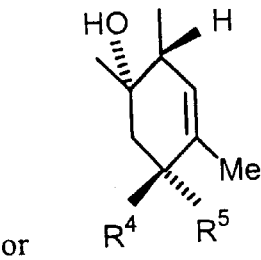
$R^5$ = hydrogen; or $R^4$, $R^5$ is =O
or
$R^2 = HOCH_2$ and A =
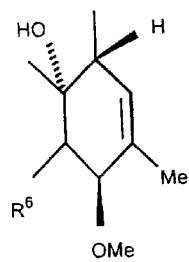
or

FIGURE 23B
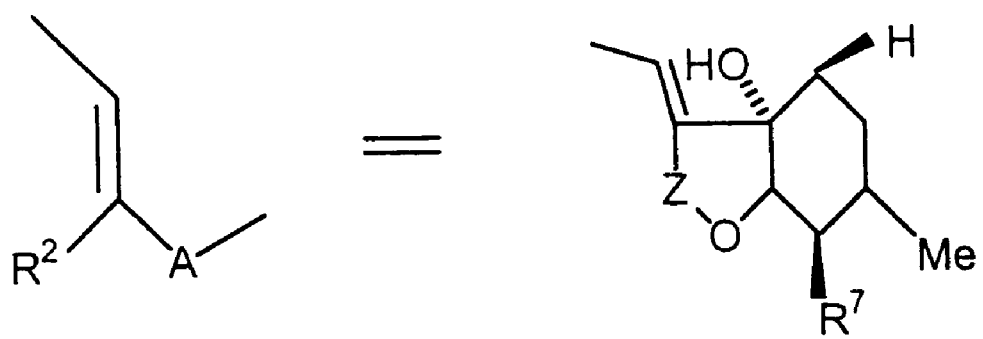
$R^7$ = OH or OCH$_3$
Z = CHOH or C=O
or
$R^1$ = hydrogen and
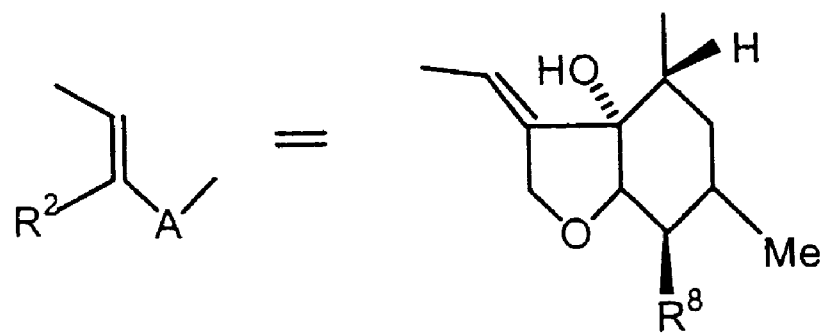
$R^8$ = OH or OCH$_3$

| R₁ | R₂ | R₃ | R₄ |
|---|---|---|---|
| OH | CH₃ | OCH₃ | CH₃ |
| hydrogen | CH₃ | OCH₃ | CH₃ |
| hydrogen | CH₃ | =O | CH₃ |
| hydrogen | CH₃ | OH | CH₃ |
| hydrogen | CH₃ | OCH₃ | CH=O |
| hydrogen | CH₃CH₂ | OH | CH₃ |

$R^1$ is OH;

A is =O or OH; and, the dashed line indicates a single or double bond.

FUNGAL EFFLUX PUMP INHIBITORS

RELATED APPLICATION

This application claims the benefit of Lomovskaya et al., U.S. Provisional Application No. 60/061,322, filed Oct. 2, 1997, entitled FUNGAL EFFLUX PUMP INHIBITORS, which is hereby incorporated by reference in its entirety, including drawings.

FIELD OF THE INVENTION

This invention relates to the field of antimicrobial agents and more specifically it relates to the use of milbemycins and analogous compounds as efflux pump inhibitors to be co-administered with antimicrobial agents to inhibit the growth of microbial cells.

BACKGROUND OF THE INVENTION

Fungal infections are relatively rare in immunocompetent humans or other mammals. A number of Candida species are often present as benign commensal organisms in the digestive system of healthy individuals (Shepherd, M et al, *Ann. Rev. Microbiol.*, 39:579–614, 1985). Fungal infections, however, can be life threatening for immunocompromised individuals. Three major groups of severely immunocompromised individuals have emerged in recent years, These are: 1) cancer patients undergoing chemotherapy, 2) organ transplant patients treated with immunosuppressive agents, and 3)AIDS patients. The frequency of fungal infections has risen world-wide in recent years. Data from the National Nosocomial Infections Surveillance System conducted in the United States showed 487 percent increase in Candida bloodstream infections between 1980 and 1989 (Reviewed in Rex, M. Rinldi, and M. Pfaller. 1995. Resistance of Candida species to fluconazole. *Antimicrob. Agents and Chemother.* 39:1–8). Oropharyngeal candidiasis was shown to be the most common fungal infection in AIDS patients. Prevalence studies have suggested that up to 90% of patients with AIDS have had at least one episode of oropharyngeal candidiasis (Powderly. 1994. Resistant Candidiasis. 1994. AIDS research and Human *Retrovirusses.* 10:925–929).

There are only a small number of therapeutic agents available for the treatment of serious fungal infections. Amphotericin B, flucytosine, fluconazole, itraconazole and ketoconazole are some of the few currently available drugs against systemic fungal infections (Odds. 1993. Resistance of yeasts to azole-derivative antifungals. *J. Antimicrob. Chemother.* 31: 463–471).

The mechanism of action of amphotericin B, a polyene macrolide antibiotic, is based on its interaction with the plasma membrane of sensitive organisms, which impairs the barrier function of the membrane. Its selectivity may be related to its greater affinity for the ergosterol of fungal membranes than for the cholesterol of mammalian membranes. Amphotericin B is a fungicidal agent. Resistance to amphotericin B is rare and is based on a marked (74–85%) decrease in the ergosterol content in resistant variants. However, amphotericin B is associated with many toxic side effects and is poorly absorbed from the gastrointestinal tract, which necessitates intravenous administration.

The mechanism of action of flucytosine (5FC) is the inhibition of DNA and RNA synthesis. 5FC is taken up by a cytosine permease. It is converted to 5-fluorouracil (5FU) by cytosine deaminase inside the fungal cell. The low activity of cytosine deaminase in mammalian cells is the basis for the low toxicity of 5FC in human. 5FU is converted into 5-fluorouridilic acid, which is further phosphorylated and incorporated into RNA. As a result of formation of such aberrant RNA the fungal growth is inhibited. 5FU is also converted to a potent inhibitor of thymidilate synthase and, as a result, inhibits DNA synthesis. Thus, 5FC is a potent fungicidal agent. However, it rapidly becomes ineffective since mutations to resistance arise with high frequency. This resistance results from loss or mutation of any of the enzymes which are involved in its conversion into toxic intermediates for RNA and DNA synthesis (Reviewed in Vanden Bossche, P. Marickal, and F. Odds. 1994. Molecular mechanisms of drug resistance in fungi. *Trends Microbiol.* 2:393–400).

Azoles (e.g., fluconazole, itraconazole and ketoconazole) are currently the most important agents for the treatment of fungal diseases. The primary mechanism of action of azole antifungals is inhibition of ergosterol biosynthesis. In azole-treated cells there is accumulation of 14α-methyl-sterols, the precursor intermediates of ergosterol. Conversion of 14α-methyl-sterols to ergosterol was shown to be dependent on cytochrome P-450. Azoles bind to P-450 and inhibit the function of this enzyme. (Reviewed in Saag and W. Dismukes. 1988. Azole antifungal agents: emphesis on new triazoles. *Antimicrob. Agents Chemother.* 32:1–8). The first oral azole which was proven to be effective in mycoses was clotrimazole. However, brief treatment with clotrimazole rapidly induces liver microsomal enzymes which increases metabolism of the drug and diminishes its antifungal activity. Another azole, miconazole, is not rapidly metabolized, but it has multiple toxic effects. As a result, it has very limited use as a topical agent for cutaneous mycoses. Ketoconazole was developed in the late 1970s. It was the first azole that could be given orally for systemic use and for some time it was the most important azole antifungal agent. It is less toxic than miconazole, however, dose-related inhibition of testosterone synthesis may result in menstrual irregularities, sexual impotence or oligospermia (Saag and W. Dismukes. 1988. Azole antifungal agents: emphasis on new triazoles. *Antimicrob. Agents Chemother.* 32:1–8). Relatively recently, two new azole, fluconazole and itraconazole, have been developed.

Fluconazole is currently the most extensively used agent for the treatment of patients with severe candidiasis. It has several advantages over the earlier azole antifungals, including ketoconazole. It has higher solubility in water, longer plasma-half-life, and relatively low toxicity. The bioavailability of fluconazole after oral administration is 90%. Between 1988 and 1993, fluconazole was used to treat over 15 million patients, including at least 250,000 AIDS patients (Hitchcock, C. A. 1993. Resistance of *Candida albicans* to azole antifungal agents. *Biochem Soc. Trans.* 21:1039–1047), and fluconazole treatment of patients with oropharyngeal candidiasis has been adopted by many clinics. (Recently licensed itraconazole is not used as extensively because of its much lower bioavailability).

Due to wide use of fluconazole for both treatment (and in many cases, this treatment is continued over long periods of time) and prophylaxis, reports of failure of therapy due to appearance of Candida which are resistant to fluconazole began to appear (reviewed in Rex, M. Rinldi, and M. Pfaller. 1995. Resistance of Candida species to fluconazole. *Antimicrob. Agents and Chemother.* 39:1–8, Vanden Bossche, P. Marickal, and F. Odds. 1994. Molecular mechanisms of drug resistance in fungi. *Trends Microbiol.* 2:393–400). Three different routes of acquisition of resistant variants were described. In the first scenario, infecting *Candida albicans* (*C. albicans*) were initially susceptible, but mutated and become resistant. Mutants resistant to fluconazole only and mutants which are cross-resistant to other azoles (ketoconazole, itraconazole) have been isolated. In the second scenario, patients were initially colonized with fluconazole resistant C. albicans. In the third scenario, the recent widespread use of fluconazole led to a rise in the prevalence of colonization and infection by other Candida species, such as Candida glabrata and Candida krusei, which are intrinsically less susceptible to fluconazole (reviewed in Odds. 1993. Resistans of yeasts to azole-derivative antifungals. J. Antimicrob. Chemother. 31: 463–471).

A limited number of studies on the mechanism of resistance to fluconazole in clinical isolates have appeared in the literature. It was shown that in one, probably exceptional case, amplification of the gene CYP51, encoding P-450 (fluconazole target) is implicated in drug resistance (Vanden Bossche, P. Marickal, F. Odds, L. Le Jeune, and M.-C. Coene. 1992. Characterization of an azole resistant Candida albicans isolate. Antimicrob. Agents and Chemother. 36: 2602–2610). In another case resistance to fluconazole was correlated with the appearance of an altered P-450 which had decreased affinity to fluconazole (Hitchcock, C. A. 1993. Resistance of Candida albicans to azole antifungal agents. Biochem Soc. Trans. 21:1039–1047). However, the majority of the cases of fluconazole resistance appears to originate from decreased accumulation of fluconazole inside the resistant cells (H. Vanden Bossche et al, 1994, F. C. Odds, 1993). Moreover, decreased accumulation of fluconazole in resistant cells was also demonstrated for the other two types of resistance described above. It was also reported that species which are intrinsically non-susceptible to fluconazole, such as C. glabrata and C. krusei, and Aspergillus fumigatus accumulate less fluconazole than C. albicans (H. Vanden Bossche et al, 1994). C. glabrata and C. krusei are much more susceptible to itraconazole, and it has been shown that these two fungal species accumulate higher levels of itraconazole than fluconazole (Marichal et al., 1995, Origin of differences in susceptibility of Candida krusei to azole antifungal agents, Mycoses 38:111–117). Thus, it appears that both the acquired resistance and the intrinsic non-susceptibility of different fungal species were due to the decreased drug accumulation in the cell. The reason for decreased drug accumulation can be either decreased uptake and/or increased efflux from the cell.

Active efflux is associated with activity of membrane transporter proteins, also known as efflux pumps. These pumps are ubiquitous from bacteria to mammals (for review, see Higgins, C. F. 1992. ABC transporters: from microorganisms to man. Annu. Rev. Cell Biol. 8:67–113). For their activity they can utilize either the energy of ATP hydrolysis (ABC-transporters superfamily) or the energy of the proton transfer (Major Facilitators, MF, superfamily). They can be specific toward a particular substrate as in the case of the TetA protein from gram-negative bacteria which effluxes tetracycline, the MsrA protein from Staphylococcus aureus (S. aureus) which effluxes erythromycin and related macrolides and the efflux pumps which extrude antibiotics from antibiotic-producing organisms.

On the other hand, there are a large number of efflux pumps which are capable of extruding from the cell a variety of structurally unrelated compounds. Many of these pumps are of considerable clinical significance: mammalian P-glycoprotein multi-drug resistant efflux pump confers resistance to cancer cells against chemotherapeutic drugs (reviewed in Gottesman, M and Ira Pastan. 1993. Biochemistry of multi-drug resistance mediated by the multidrug transporter. Annu. Rev. Biochem 62:385–427), Pgh1 has a role in the chloroquine resistance of the malaria parasite (Borst and M. Quelette. 1995. New mechanisms of drug resistance in parasitic protozoa. Annu. Rev. Microbiol. 49:427–60), Mex pumps confer resistance to Pseudomonas aeruginosa (P. aeruginosa) against quinolones and many others structurally unrelated antibiotics (reviewed in Nikaido, 1994, Prevention of drug access to bacterial targets: permeability barriers and active efflux, Science 264:382–388). Recently, multiple-drug resistant (MDR) pumps were implicated in fluconazole resistance in both C. albicans and C. glabrata (Parkinson et al. 1995. Fluconazole resistance due to energy-dependent drug efflux in Candida glabrata. Antimicrob. Agents Chemother. 39:1696–1699; Sanglard et al. 1995. Mechanisms of resistance to azole antifungal agents in Candida albicans isolates from AIDS patients involve specific multidrug transporters. Antimicrob. Agents Chemother. 39:2378–2386; Albertson et al. 1996. Multiple efflux mechanisms are involved in Candida albicans fluconazole resistance. Antimicrob. Agents Chemother. 40:2835–2841).

The information provided and the references cited herein are not admitted to be prior art to the present invention, but are provided solely to assist the understanding of the reader.

SUMMARY OF THE INVENTION

This invention is concerned with the use of the milbemycins and related compounds as efflux pump inhibitors and methods for treating microbial infections or cancer or other condition using the milbemycins and related compounds. Particularly appropriate examples of such microbial infections are infections caused by pathogenic fungal species, Candida albicans, Candida glabrata, and Candida krusei which are resistant to many of the commonly used antifungal agents, such as a variety of azoles. While C. albicans, C. glabrata, and C. krusei are examples of appropriate fungi, other fungal and microbial species may contain similar broad substrate efflux pumps, which actively export a variety of antimicrobial agents, and thus are also appropriate targets. The invention further concerns the identification and use of efflux pump inhibitors targeted to a CDR1, CDR2, BEN, or FLU1 efflux pump or a homolog of such a pump.

The term "efflux pump" refers to a protein assembly which exports substrate molecules from the cytoplasm or periplasm of a cell, in an energy dependent fashion. An "efflux pump inhibitor" is a compound which specifically interferes with the ability of an efflux pump to export its normal substrate or other compounds such as antimicrobial agents. Efflux pump inhibitors are useful, for example, for treating microbial infections by reducing the export of a co-administered antimicrobial agent. Thus, a microbe which can efflux an antimicrobial agent is resistant to the inhibiting effect of the antimicrobial agent, and becomes sensitive to the inhibiting effect of the same antimicrobial agent in the presence of an efflux pump inhibitor. An efflux pump inhibitor is thus distinguished from generally toxic compounds, general metabolic poisons, energy uncouplers, or other such compounds which have many direct inhibitory effects in a cell. It is recognized that an efflux pump inhibitor may have additional indirect effects as inhibition of efflux pump activity alters the intracellular levels of certain species of compounds or ions.

In connection with efflux pumps, the term "homolog" refers to another efflux pump which has significant amino acid sequence homology as determined by optimized alignment comparison of the polypeptide sequence or sequences from the homolog with the reference efflux pump polypeptide sequence or sequences. Those skilled in the art are familiar with such methods and with the computer programs generally used for performing such comparisons. Preferably the homolog has at least 20% amino acid sequence identity, more preferably at least 30%, or preferably at least 30%, or at least 40% sequence similarity, and more preferably at least 50%, as determined using any widely accepted sequence analysis method as known to those skilled in the art.

The term "milbemycin" or "milbemycins" refers to a group of sixteen-membered macrolactones containing a fused spiro ether moiety, for example, compounds of the type isolated from the fermentation of Streptomyces hygroscopicus NRRL 5739, as referenced below. Milbemycins have been described as having insecticidal, acaracidal, and anthemlmintic activity. A variety of other milbemycins and milbemycin-type compounds are described herein and in references listed below. Yet others are known to those skilled in the art.

The term "milbemycin-type compound" refers to compounds and families of compounds structurally related to milbemycins which are also sixteen-membered macrolactones containing a fused spiro ether moiety and which also have efflux pump inhibitory activity. Such compounds also generally have insecticidal, acaracidal, or anthelmintic actitities. Such compounds have been isolated from the fermentation of microorganisms, and include compounds modified from such natural products by chemical modification. Thus, these compounds include milbemycins, compounds structurally related to milbemycins, and derivatives of such compounds. Preferred milbemycin-type compounds are not avermectins.

In connection with the milbemycin-type compounds, the term "derivative" refers to a compound which has been chemically modified from another milbelycin or milbemycin-type compound by the addition, substitution, or modification of a substituent of the starting compound, and which retains or has gained efflux pump inhibitory activity. Examples of preferred substituents are given in certain of the references cited herein in connection with milbemycin-type compounds.

In a first aspect, the invention provides a method for inhibiting the growth of cells, preferably inhibiting growth of a microbe, preferably a fungus, by contacting the microbe with a milbemycin or milbemycin-type compound or derivative, preferably with a milbemycin or derivative, and a second compound. The milbemycin or milbemycin-type compound enhances the susceptibility of the cells, e.g., the microbe, to the second compound. Preferably the second compound is an antimicrobial agent, such as an antifungal agent, for example, an azole such as fluconazole, or terbinafine. Preferably the milbemycin or milbemycin-type compound or derivative is active on at least one of a CDR1, CDR2, BEN, or FLU1 efflux pump or a homolog of such a pump. In preferred embodiments, the compound is active on a plurality of those efflux pumps.

In preferred embodiments, the cells can be contacted with the milbemycin or milbemycin-type compound or derivative and the second compound simultaneously or can be contacted serially.

The cells can be of a variety of different types, so long as the milbemycin or milbemycin-type compound enhances the susceptibility of the cells to the second compound. For example, the cells can be animal cells, e.g., human cells, lower eukaryotic cells, or prokaryotic cells. In preferred embodiments, the cells are of a microbe, preferably a fungus, such as a Candida species, for example, *Candida albicans, Candida krusei*, or *Candida glabrata*. In preferred embodiments, the cells are mammalian cells, e.g., human cells, which preferably express P-glycoprotein. The cells may be cancer cells, in which case the second compound is preferably an anticancer agent.

The term "microbe" is used in its usual biological sense to refer to very small organisms, which generally are only readily observable when viewed under a microscope or when aggregated. Thus, the organism is generally of less than 1 mm in average dimension, more typically less than 100 $\mu$m, and often less than 10 $\mu$m. However, it is understood that certain microbes have such size only during certain stages of the life cycle. The term "microbe" is also meant to include fungi which have a mycelial vegetative stage. In this case, the term "microbial cell" can refer to a coenocytic or mycelial structure, which is generally polynucleate. Thus, the term "microbe" includes, for example, bacteria, algae, fungi, and protozoans.

The terms "fungus" and "fungi" refer to lower eukaryotic organisms as generally understood by those skilled in the art. Commonly fungi have a mycelial or coenocytic vegetative stage. However, in the context of this invention, unless specifically indicated to the contrary, included are the yeasts (e.g., Saccharomyces species). In this context, "yeast" refers to a lower eukaryotic organism which has a single celled growth stage and is classified within the fungi, for example, based on properties such as cell structure, reproductive mechanisms, nucleic acid sequence comparisons or other characteristics commonly utilized for classifying organisms. The fungi include the following classes: Zygomycetes, Ascomycetes, the Basidiomycetes, Deuteromycetes, and Oomycetes.

The invention encompasses, in the various aspects, the use of a variety of milbemycins and milbemycin-type compounds. In particular embodiments, these include compounds described by the structures provided below and compounds described in the references indicated below in connection with compounds appropriate for this invention. These include, for example, the S-541 compounds, the LL-F28249 compounds, the N787-182 compounds, and the VM series compounds. These groups of compounds are identified in the references cited below and in the attached figures. In addition, further chemical derivatives of these compounds which retain efflux inhibiting activity are within the scope of this invention.

The second compound is generally selected to be one which has a phamacologic activity in the cell. Thus, in embodiments where the cell is a mammalian cell, e.g., a human cell, the second compound can be an anticancer agent. Clearly, this is most appropriate where the mammalian cells are cancer cells. Likewise, where the cells are microbial cells, e.g., fungal cells, the second compound can be an antimicrobial agent, e.g., an antifungal agent.

In general, the method involves the inhibition of an efflux pump by the milbemycin or milbemycin-type compound in a case where the efflux pump would otherwise export the second compound. Thus, in preferred embodiments, the method is used in connection with a microbe or other cell which is resistant to the second compound, as the milbemycin or milbemycin-type compound will enhance the susceptibility of the cell for that second compound.

In this context, the term "resistant" refers to cells, e.g., fungi, which are not susceptible to the effects of a particular compound such as an antifungal or anticancer agent. Resistance can be intrinsic or acquired. Intrinsic resistance is the naturally occurring resistance that is found among most or all members of an entire species of organism, e.g., microorganism. Acquired resistance occurs through mutations of existing DNA or acquisition of new DNA in a previously susceptible organism. For example, antimicrobial agents may exert selective pressure for selection of acquired resistance. Both intrinsic and acquired resistance may be mediated by a variety of different mechanisms. A mechanism of particular interest in the present invention is resistance mediated by efficient export of potentially therapeutic agents, e.g., antimicrobial agents, from the cell, e.g., microbial cell. Thus, a resistant cell can be identified as one which is less susceptible to a particular therapeutic compound (e.g., antimicrobial agent or anticancer agent) than is a cell which does not contain a particular cellular mechanism for reducing the susceptibility of the cell to that compound. Thus, for example, for resistance mediated by expression of one or more efflux pumps which export a particular compound, the resistant cell can be identified by comparison of the susceptibility of the cell for the compound as compared to an otherwise isogeneic cell which does not express a functional efflux pump which exports the compound. Preferably, but not necessarily, a resistant cell is at least 2-fold, more preferably at least 4-fold, and most preferably at least 8-fold less susceptible to effects of a compound than are cells which are isogeneic except for the absence of the corresponding functional resistance mechanism or mechanisms.

The milbemycin or milbemycin-type compound can be prepared in various ways. These include the isolation of a natural product, such as isolation from a fermentation of one of the strains identified in the references listed below. As understood by those skilled in the art, certain of the compounds may be prepared by directed biosynthesis. In addition, the milbemycin or milbemycin-type compound can be prepared by chemical modification or microbial transformation of a naturally-occurring milbemycin or milbemycin-type compound. Likewise, the milbemycin or milbemycin-type compound can be prepared by chemical synthesis.

"Directed biosynthesis" refers to a method for causing biosynthesis of a product or products by the addition of an appropriate biosynthetic precursor or inhibitor of a particular biosynthetic pathway to a microbial fermentation. This causes the microorganism to incorporate the added precursor into a secondary metabolite (e.g., a milbemycin) it normally produces or to change the chemical structure of the secondary metabolite by omitting some biosynthetic step which would normally be performed. Milbemycin-type compounds which result from such directed biosynthesis are within the scope of this invention.

"Microbial transformation" refers to the modification of the structure of a chemical compound (e.g., a milbemycin-type compound) by the fermentation process of a microorganism. Such transformations are known in the art, and are described, for example, in Chen, EP 369,502, EP 475,518, and EP 478,064. Milbemycin-type compounds which result from such transformation are within the scope of this invention.

In a related aspect or in embodiments of the above aspect, the invention provides a method for inhibiting the growth of a mammalian cell by contacting the cell with a milbemycin or milbemycin-type compound and a second compound. Similar to the microbial cells as described above, the milbemycin or milbemycin-type compound enhances the susceptibility of the cell to the second compound. This method is particularly applicable to inhibition of growth of a cancer cell, preferably where the second compound is an anticancer agent. This is particularly useful when the cancer cell is resistant to the anticancer agent. In particular it was shown that the milbemycin-type compounds inhibit the activity of P-glycoprotein, and thus the method is preferably used to inhibit the growth of cells which express or overexpress P-glycoprotein.

Also, as indicated above, the methods of inhibiting cells, methods of treatment, compositions, and methods of preparing compositions of this invention can use a variety of milbemycins or milbemycin-type compounds, such as those described below.

Such appropriate compounds include milbemycin-type macrolides of Structures (I), (II), and (III)

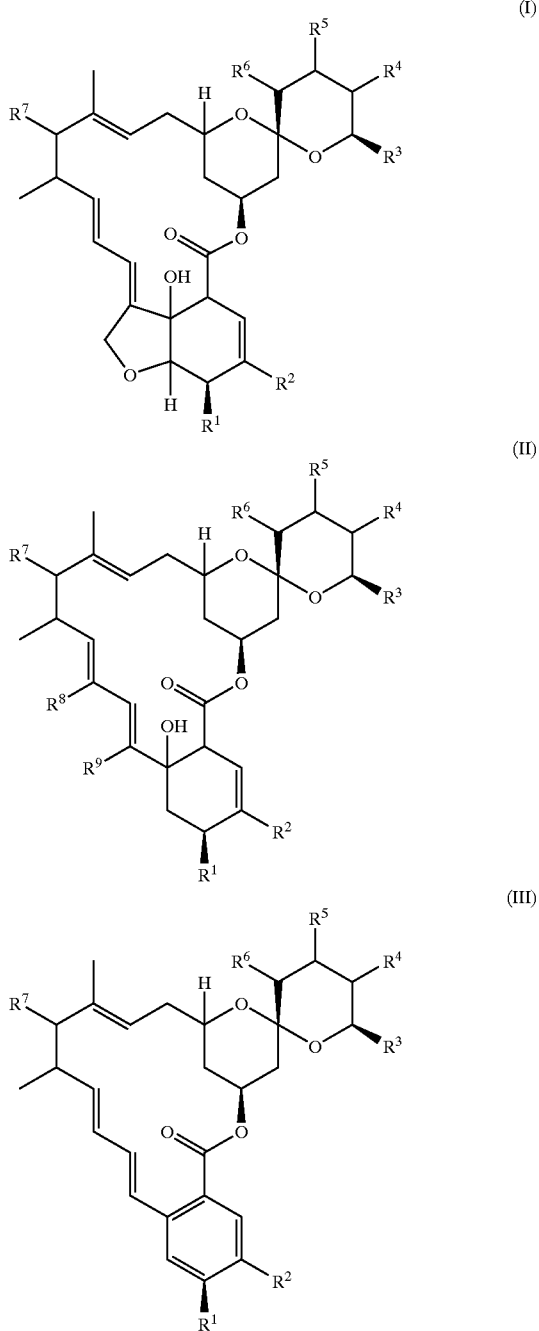

Where independently
for Structures I and II $R^1$=O, OH, $OCH_3$;
for Structure III $R^1$=OH;
$R^2$=$CH_3$, $CH_2OCOCH_2CH_2CH_3$, $CH_2OCOCH(CH_3)_2$, $CH_2OCOCH_2CH_2CH_2CH_3$, $CH_2OCOCH_2CH(CH_3)_2$, $CH_2OCOCH_2CH(CH_3)CH_2CH_3$, $CH_2OCOCH_2CH(CH_2CH_3)_2$, $CH_2OCOCH=CHCH_3$, $CH_2OCOCH=C(CH_3)_2$, $CH_2OCOCH=C(CH_3)(CH_2CH_3)$, $CH_2OCOCH=C(CH_2CH_3)_2$, $CH_2OCOC(CH_3)=CHCH_3$, $CH_2O_2CCH_2C_6H_5$, or

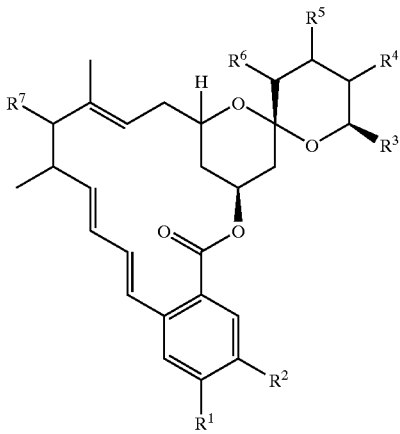

(III)

$R^3=CH_3$, $CH_2CH_3$, $CH(CH_3)_2$, $CH_2C(CH_3)CH_2CH_3$, $C(CH_3)=CH(CH_3)$, $C(CH_3)=CH(CH_2CH_3)$, $C(CH_3)=CH(CH(CH_3)_2)$, $C(CH_3)=CH(CH_3)$;

$R^4=CH_3$, $CH_2CH_3$;

$R^5=H$, $OH$, $OCOCH(CH_3)_2$, $OCOCH(CH_3)Bu^n$, $OCOC_4H_9$; $OCOC_6H_{13}$;

$R^6=H$, $OH$;

$R^7=H$, $OH$, $OCOCH(CH_3)_2$, $OCOCH_2CH(CH_3)_2$;

for Structure II $R^8=CH_3$, $CH_2OH$, $CHO$;

$R^9=H$, $OH$.

Further, the following macrolide antibiotics, milbemycins (also referenced as B-41 compounds) (*J. Antibiotics,* 33:1120–1127, 1980; *J. Antibiotics,* 36:980–990, 1983; Acki et al, U.S. Pat. No. 3,950,360, 1976, U.S. Pat. No. 3,992,551, 1976), the S-541 compounds (*Tetrahedron Lett,* 28:5353–5356, 1987; Eur. Pat. Appl. 242,052, 1987; Ward et al., Brit. Pat. 2,166,436, 1986), the LL-F28249 compounds (*J. Antibiotics,* 41:519–529, 1988; Carter et al, U.S. Pat. No. 5,106,994, 1992; U.S. Pat. No. 5,169,956, 1992), the N 787-182 compounds (*J. Antibiotics,* 45:659–670, 1992; Haxell et al., Eur. Pat. Appl. 334,484, 1989;), and the VM series compounds (*J. Antibiotics,* 43:1069–1076, 1990; *J. Antibiotics,* 49:272–280, 1996; Banks et al, Eur. Pat. Appl. 254,583, 1987; Banks et al., Eur. Pat. Appl. 325,462, 1989) are efflux pump inhibitors and can be utilized in embodiments of the various aspects of this invention.

Additional milbemycins and milbemycin-type compounds and derivatives appropriate for use in this invention are described in the following patents and publications:

DE 3916931 A1, 1990, Sollner et al.
GB 2,170,499 B, 1985, Poole et al.
EP 242,052 A, 1987, Rudd et al.
GB 2,187,742, 1987, Ramsay et al.
AU 23,602, 1988
EP 298,423 A, 1988, Katoh et al.
EP 204,421 A, 1986, Goegelman
EP 205,251 A, 1986, Goegelman
EP 300,674 A, 1989, Chen
EP 369,502 A, 1989, Chen
EP 475,518 A, 1991, Arison et al.
EP 511,881 A, 1992, Goegelman et al.
EP 478,064 A, 1991, Shumanov and White
EP 308,145 A, 1989, Dutton and Perry
EP 410,615 A, 1990, Hiroshi et al.
JP 63-264484, 1988
JP 63-227590, 1988
*Tetrahedron Lett,* 28:5353–5356, 1987, Ramsay et al.
*J. Antibiotics,* 43:1321–1329, 1990, Nakagawa et al.
U.S. Pat. No. 5,030,650
U.S. Pat. No. 4,916,154
U.S. Pat. No. 4,886,829
EP 280,928
U.S. Pat. No. 5,149,832
U.S. Pat. No. 4,988,824
GB 2,167,751
U.S. Pat. No. 4,547,520
AU 8,317,168
EP 444,964
U.S. Pat. No. 4,093,629
U.S. Pat. No. 4,134,973
U.S. Pat. No. 4,144,352

The structures of some of the compounds described in the above references are shown in the attached figures. The references cited above dealing with milbemycins and milbemycin-type compounds and derivatives are further indicative of the level of skill in the art concerning obtaining and modifying those compounds. In particular, the references provide source organisms, fermentation methods and conditions, and purification methods, as well as modification processes, as known to those skilled in the art.

Compounds prepared by semi-synthetic modifications, enzymatic modifications and microbial transformations of the compounds described in the above patents and publications are also appropriate for use in this invention. Compounds prepared by directed biosynthesis using the producing strains which produce the compounds described in the above patents and publications are also within the scope of this invention.

In the context of cell growth, the term "inhibit" means that the rate of growth of the cell, e.g., the microbial population, is decreased. Such inhibition can be monitored, for example, by the difference in turbidity of liquid cultures in the presence or absence of the inhibiting agent, or by the difference in plaque size for cultures on solid media in the presence or absence of the inhibiting agent, or by other methods well-known to those skilled in the art.

In reference to the presence of a specific efflux pump in a fungus (similarly for other microbes or cells), the term "overproduces" refers to the presence in that fungus of a significantly larger number of the specific efflux pump than is found in most naturally occurring (usually non-hospital varieties) isolates of that fungal species. The term does not refer merely to the production of a large number of the component polypeptides of an efflux pump, but rather to the presence of a larger number of functional efflux pumps in the membranes of the cell. Consequently, a fungal cell which overproduces an efflux pump, will export the substrate molecules more efficiently than a strain of that fungus which does not overproduce the efflux pump.

A fungal strain which overproduces an efflux pump, is thus in contrast to a "wild-type strain". A wild-type strain produces a specific efflux pump at a level which is typical of natural isolates of that fungal species. More importantly, however, a wild-type strain produces a specific efflux pump at a level which is significantly lower than a related strain which overproduces that specific efflux pump.

As used herein, the term "antifungal agent" refers to a compound which specifically inhibits the growth of a fungus. More generally, the term "antimicrobial agent" refers to a compound which specifically inhibits the growth of a microbe, thus the explanation of this term applies also to other microbes and antimicrobial agents. Thus such agents may have either fungicidal or fungistatic activity. In general, if an antifungal agent is fungistatic, it means that the agent essentially stops fungal cell growth (but does not kill the fungus); if the agent is fungicidal, it means that the agent kills the fungal cells (and may stop growth before killing the fungus). However the term specifically distinguishes compounds which are generally toxic to cells. Some examples of different classes of antifungal agents are amphotericin B, flucytosine, azoles such as fluconazole, itraconazole, and ketoconazole, and terbinafine. The efflux pump inhibitors of this invention may be antimicrobial (e.g., antifungal) agents when used alone, and/or they may potentiate the activity of another antimicrobial agent (increase the susceptibility of the microbe for that other antimicrobial agent).

A "sub-inhibitory concentration" of an inhibitor, e.g., an antifungal agent, is a concentration which is greater than zero, but less than the concentration which would inhibit the majority of the cells in a population, e.g., a fungal population, of that specific fungal strain. (Similarly for other microbes.) In general, a sub-inhibitory concentration of an antifungal agent (or antimicrobial agent) is a concentration less than the Minimum Inhibitory Concentration (MIC).

In a related aspect, this invention provides a method for treating a microbial infection, preferably a fungal infection, in an organism, such as in an animal or a plant. Animals specifically include mammals, e.g., humans. The methods involves treating an animal or other organism bearing or suffering from such an infection with an antimicrobial agent, preferably an antifungal agent, and an efflux pump inhibitor which increase the susceptibility of the microbe, e.g., fungus, for that agent (e.g., antifungal agent). In this way, in the case of a fungal infection, a fungus involved in the infection can be treated using the antifungal agent in smaller quantities, or can be treated with an antifungal agent which is not therapeutically effective when used in the absence of the efflux pump inhibitor. Thus, this method of treatment is especially appropriate for the treatment of infections involving fungal strains which are difficult to treat using an antifungal agent alone due to a need for high dosage levels (which can cause undesirable side effects), or due to lack of any clinically effective antifungal agents. However, it is also appropriate for treating infections involving microbes which are susceptible to particular antifungal agents as a way to reduce the dosage of those particular agents. This can reduce the risk of side effects, but can also reduce the selection effect for highly resistant microbes resulting from the consistent high level use of a particular antifungal agent. In particular embodiments, various antifungal agents, including the azole class of antifungal agents, can be used. In particular embodiments an antibiotic of the above classes can be, for example, one of the following: terbinafine or an azole antimicrobial agent such as fluconazole, itraconazole, ketoconazole.

In a further related aspect, this invention includes a method for prophylactic treatment of an animal, preferably a mammal, or other organism. In this method, an antimicrobial agent, e.g., an antifungal agent, and an efflux pump inhibitor as described above is administered to an animal or other organism at risk of a microbial infection, e.g., a fungal infection, or for which it is desirable to prevent the establishment of a microbe, e.g., a fungus.

In the context of the response of a microbe (or other cell), such as a fungus, to an antimicrobial agent, the term "susceptibility" refers to the sensitivity of the microbe for the presence of a compound such as an antimicrobial agent. So, stated in the context of microbes, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

In another related aspect, the invention provides a method for treating a mammal, e.g., a human, suffering from a cancer by administering a milbemycin or milbemycin-type compound or derivative as described above and a second compound as described for inhibiting the growth of a cancer cell above.

As used herein, the term "treating" refers to administering a pharmaceutical composition for prophylactic and/or therapeutic purposes. The term "prophylactic treatment" refers to treating an organism, such as a human patient, who is not yet infected, but who is susceptible to, or otherwise at risk of, a particular infection. The terms "susceptible" and "at risk" do not refer to the status of organisms of that type generally, but rather refers to a significantly enhanced risk. Such risk may, for example, be due to a specific exposure to a particular potentially infective agent, to a generally weakened physical condition, or immune system deficiency. Preferably, for humans, the enhanced risk is sufficient such that a prudent doctor familiar with the treatment of the potential infection would find prophylactic treatment medically warranted. The term "therapeutic treatment" refers to administering treatment to a patient already bearing or suffering from an infection. Thus, in preferred embodiments, "treating" is the administration to a mammal (either for therapeutic or prophylactic purposes) of therapeutically effective amounts of an efflux pump inhibitor preferably in combination with a second compound, e.g., an antifungal (or antimicrobial) agent in combination (either simultaneously or serially).

By "therapeutically effective amount" or "pharmaceutically effective amount" is meant amounts individually of an efflux pump inhibitor and/or a second compound, such as an antimicrobial agent, as disclosed for this invention, which have a therapeutic effect, which generally refers to the inhibition to some extent of the normal metabolism of partiuclar cells, such as microbial cells causing or contributing to a microbial infection. The doses of efflux pump inhibitor and antimicrobial agent (or similarly efflux pump inhibitor and anticancer agent) which are useful in combination as a treatment are therapeutically effective amounts. Thus, as used herein, a therapeutically effective amount means those amounts of efflux pump inhibitor and/or antimicrobial agent (or other second compound) which, when used in combination, produce the desired therapeutic effect as judged by clinical trial results and/or model animal infection studies. In particular embodiments, the efflux pump inhibitor and antimicrobial agent (or other second compound) are combined in predetermined proportions and thus a therapeutically effective amount would be an amount of the combination. This amount and the amount of the efflux pump inhibitor and second compound (e.g., antimicrobial agent) individually can be routinely determined by one of skill in the art, and will vary, depending on several factors, such as the particular cells or microbial strain involved and the particular efflux pump inhibitor and second compound (e.g., antimicrobial agent) used. This amount can further depend upon the patient's height, weight, sex, age and medical history. For prophylactic treatments, a therapeutically effective amount is that amount which would be effective if a microbial infection existed or other condition to be treated existed (e.g., a cancer).

A therapeutic effect relieves, to some extent, one or more of the symptoms of the infection or other condition, and includes curing an infection or other condition. "Curing" means that the symptoms of active infection or condition are eliminated, including the elimination of excessive numbers of viable microbes of those involved in the infection or of other cells involved in causing a condition in which the elimination or reduction of certain cells is desirable. However, certain long-term or permanent effects of the infection or condition may exist even after a cure is obtained (such as extensive tissue damage).

The term "microbial infection" refers to the presence of a microbe in or on tissues of a host animal, e.g., a mammal. Preferably, but not necessarily, this will be the presence of pathogenic microbes. It can include the growth of microbes which are normally present in or on the body of a mammal, preferably including cases of excessive growth, and other situations where the elimination of the presence of the microbe is desirable (e.g., sub-clinical infections) (or prevention of establishment of the presence of the microbe). Usually, but not necessarily, a microbial infection will be a situation in which the presence of a microbial population(s) is damaging or potentially damaging to a host mammal. Thus, an animal is "suffering" from a microbial infection when excessive numbers of a microbial population are present in or on the animal's body, or when the effects of the presence of a microbial population(s) is damaging the cells or other tissue of a mammal. As an example, this description specifically applies to a fungal infection.

The term "bearing a microbial infection" indicates that a particular microbial population is present in or on the body of an animal. It is not necessary that the presence of the microbes be damaging to the animal.

The term "administration" or "administering" refers to a method of giving a dosage of an antimicrobial pharmaceutical composition to a mammal, where the method is, e.g., topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

The term "mammal" is used in its usual biological sense. Thus, it specifically includes humans, dogs, and cats, but also includes many other species. The term "warm-blooded animal" has its usual biological meaning.

In a related aspect, the invention also provides methods of inhibiting growth of a microbe, e.g., a fungus, by contacting the microbe with an efflux pump inhibitor active on a CDR1, CDR2, BEN, or FLU1 efflux pump or a homolog thereof. Preferably the microbe is also contacted with an antimicrobial, e.g., antifungal agent. In preferred embodiments, the microbe, efflux pump inhibitor, anti microbial agent pharmaceutical compositions, and method of contacting are as described for aspects above or otherwise described herein.

Likewise, in another related aspect, the invention provides a method for prophylactic or therapeutic treatment of a microbial infection of an organism, e.g., a plant or an animal such as a mammal like a human, by administering to the organism a therapeutic amount of an efflux pump inhibitor, where the efflux pump inhibitor is effective to inhibit the activity of at least one of a CDR1, CDR2, BEN, or FLU1 efflux pump or homolog, and preferably of a plurality of such pumps. Preferably, an antimicrobial agent is also administered. Preferred embodiments involve microbes, antimicrobial agents, efflux pump inhibitors, methods of administering the compounds, pharmaceutical compositions, and organisms to be treated as described for aspects above or otherwise described herein.

Stating that the efflux pump inhibitor is "effective to inhibit the activity" of an efflux pump means that the compound at least slows the efflux pump action of the pump in a specific manner, but does not imply that every activity of the pump or of a pump component is necessarily inhibited.

In another related aspect, the invention provides a pharmaceutical composition which includes a milbemycin-type compound and a pharmaceutically acceptable carrier or excipient, where the composition is formulated for administration in conjunction with an antimicrobial agent. Thus, the antimicrobial agent may be separate or may be included in the pharmaceutical composition. In preferred embodiments, the milbemycin-type compound is a compound as indicated in the aspects described above.

Also, in preferred embodiments, the pharmaceutical composition includes an antimicrobial agent, preferably an antifungal agent, preferably an azole antifungal agent, e.g., fluconazole, itraconazole, and ketoconazole, or terbinafine, which is effluxed by an efflux pump which can be inhibited by a milbemycin or milbemycin-type compound in the composition.

In further related aspects, the invention provides a formulation or pharmaceutical composition which includes a milbemycin-type compound and an antimicrobial agent. In preferred embodiments, the milbemycin-type compound is a compound as described above. Also in preferred embodiments, the antimicrobial agent is an antifungal agent, preferably fluconazole, itraconazole, ketoconazole, or terbinafine.

In another aspect, the invention provides a method of screening for efflux pump inhibitors by determining whether the growth of a microbial strain is inhibited to a greater extent in the presence of a combination of a test compound and a sub-inhibitory concentration of an antimicrobial agent than in the presence of the sub-inhibitory concentration of the antimicrobial agent alone. The microbial strain expresses an efflux pump (at least one) which exports the antimicrobial agent, and the efflux pump is a CDR1, CDR2, BEN, or FLU1 efflux pump or a homolog of one of those pumps or a plurality of such pumps. The microbes are cultured under conditions (including a sub-inhibitory concentration of an antimicrobial agent) such that the microbes will grow unless inhibited by the presence of the test compound. Thus, a reduction in growth of the strain in the presence of the test compound as compared to the absence of the test compound is indicative that the test compound is an efflux pump inhibitor.

In preferred embodiments, the microbial strain is a recombinant *Saccharomyces cerevisiae* strain, for example, a strain expressing a recombinant CDR1, CDR2, BEN, or FLU1 efflux pump from *Candida albicans*. Also in preferred embodiments, the microbial strain is a fungal strain, such as a Candida species, for example, *Candida albicans*. In other preferred embodiments, the microbial strain overexpresses one or more of the efflux pumps. In addition, while the screening method can be carried out using a variety of different antimicrobial agents, in preferred embodiments, the antimicrobial agent is fluconazole.

In another aspect, the invention provides a method for preparing a pharmaceutical composition by identifying an efflux pump inhibitor. The identification includes screening for a compound active on a CDR1, CDR2, BEN, or FLU1 efflux pump or a homolog. The screening can, for example, be performed by the above screening method. A compound identified through such screening may be used directly in following steps, or may be used as a hit compound which is used in medicinal chemistry to prepare and identify a compound having more desirable therapeutic properties. A compound so identified is synthesized in an amount sufficient to provide a therapeutic effect when administered to an animal suffering from a microbial infection where the efflux pump inhibitor enhances the susceptibility of the microbial cells to an antimicrobial agent, preferably an antimicrobial agent for which the efflux pump inhibitor has been shown to enhance the susceptibility of cells. The method can also involve combining the efflux pump inhibitor with an antimicrobial agent and/or with a pharmaceutially acceptable carrier or excipient. The identification can, for example, involve microbial cells and/or antimicrobial agents as otherwise described herein. For example, an antimicrobial agent can be terbinafine or an azole antimicrobial agent such as fluconazole, itraconazole, or ketoconazole.

Other features and advantages of the invention will be apparent from the following Detailed Description of the Preferred Embodiments and the accompanying drawing and from the claims.

BRIEF DESCRIPTION OF THE DRAWINGS

FIG. 6B shows the structures of milbemycin-type compounds described in Takiguchi et al., *J. Antibiotics* 33:1120 (1980).

FIG. 10 shows the structures of milbemycin-type compounds (certain VM compounds) described in Baker et al., *J. Antibiotics* 43:1069 (1990), which are also described in European patent application 0 254 583 A2.

FIG. 11 shows the structures of milbemycin-type compounds (LL-F28249 compounds) described in U.S. Pat. No. 5,169,956, issued Dec. 8, 1992.

FIG. 13 shows the structures of milbemycin-type compounds described in European patent application 0 478 064 A2.

FIG. 14 shows the structures of a milbemycin-type compound produced by microbial transformation described in European patent application 0 475 518 A1.

FIG. 19 shows the structures of milbemycin-type compounds related to S541 and LL-F28249 compounds described in European patent application 0 308 145 A2. In the compound shown, R is hydrogen and $R^1$ is hydroxy or R and $R^1$ taken together are an oxo (=O); $R^2$ is a $C_3$-$C_8$ straight or branched-chain alkyl, alkenyl or alkynyl group, which may optionally contain an oxygen or sulfur atom as part of the chain, or $R^2$ may be a $C_3$-$C_8$ cycloalkyl or cycloalkenyl group or a 3- to 6-member oxygen or sulfur containing heterocyclic ring which may be saturated or fully or partially unsaturated and which may optionally be substituted with one or more $C_1$-$C_4$ alkyl groups or halogen atoms; $R^3$ is methyl or ethyl, $R^4$ is hydrogen or methyl, $R^5$ is hydrogen or hydroxy and $R^6$ is methyl or hydroxymethyl or $R^5$ and $R^6$ taken together form an —O—$CH_2$-group; $R^7$ is hydrogen, metehyl or ethyl; and $R^8$ is hydrogen or halogen; with the proviso that, when $R^2$ is a branched alkyl it is not isopropyl.

Formula II, in which $R^2$ and $R^4$ are as defined above, depicts a preferred subgenus of this particular class of compounds. Particularly preferred are compounds of Formula II in which $R^2$ is (1-methylthio)ethyl, 2-pent-4-enyl or 2-butyl.

Figure 1:
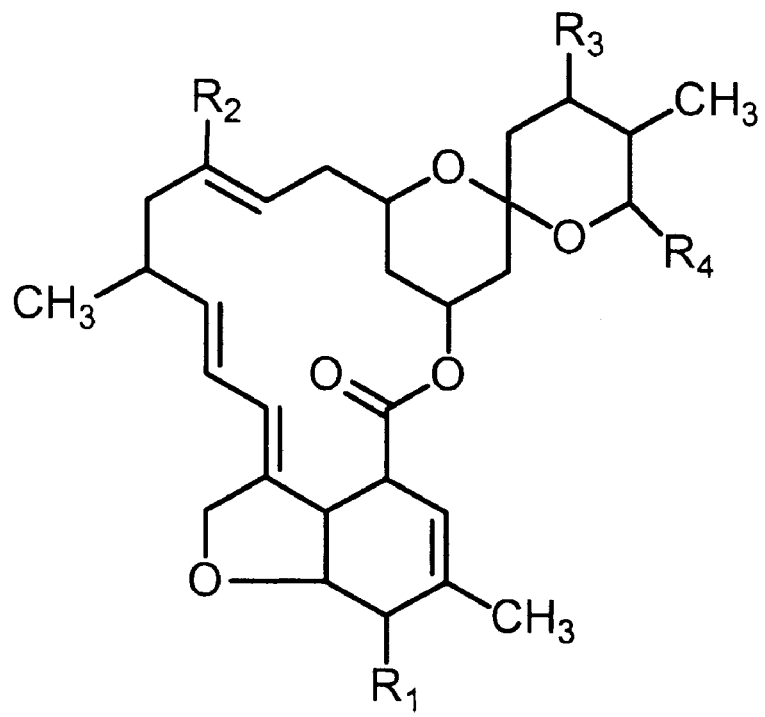
FIG. 1 shows the structures of milbemycin-type compounds described in Japan patent application JP 63-227590.
Figure 2:
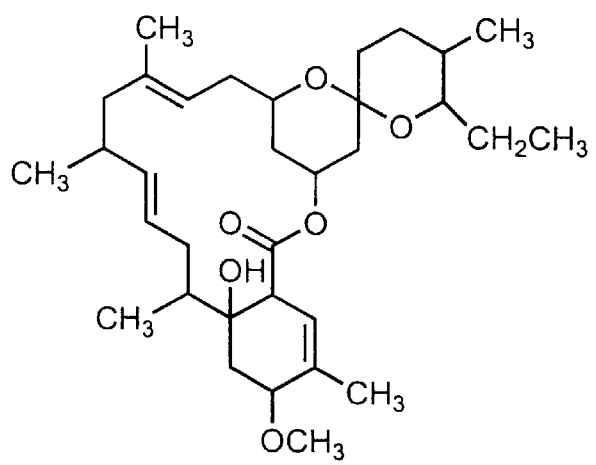
FIG. 2 shows the structures of milbemycin-type compounds described in UK patent GB 2 170 499 B.
Figure 3:
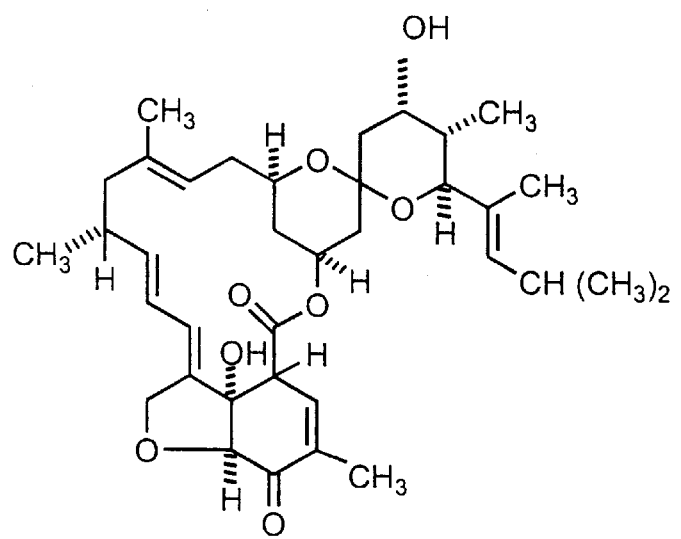
FIG. 3 shows the structures of milbemycin-type compounds described in UK patent application GB 2 187 742 A.
Figure 4:
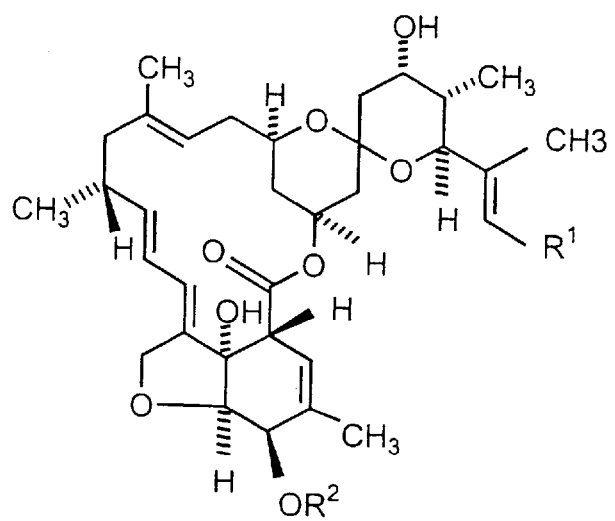
FIG. 4 shows the structures of milbemycin-type compounds (S541 compounds) described in UK patent application GB 2 166 436 A.
Figure 5:
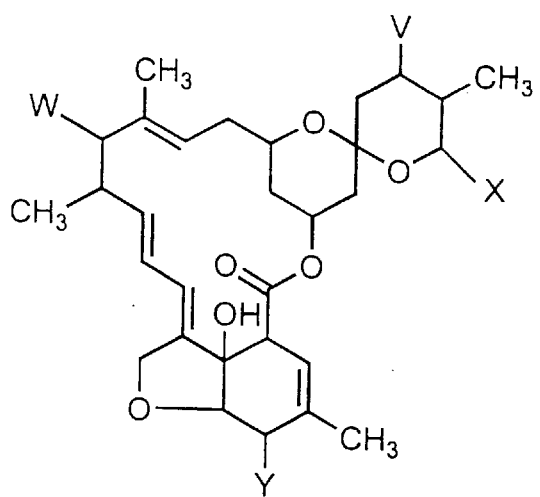
FIG. 5 shows the structures of milbemycin-type compounds described in Japan patent application 63-264484.
Figure 6A:
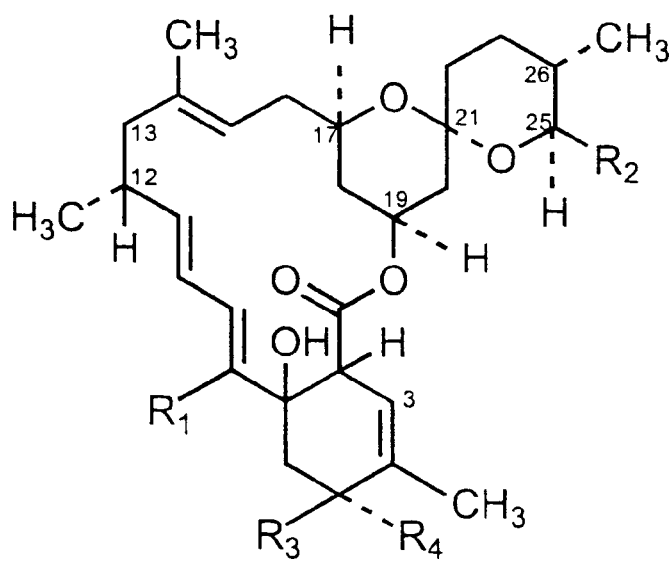
FIG. 6A shows the structures of milbemycin-type compounds described in Mishimia et al., *J. Antibiotics* 36:980 (1983).
Figure 1:
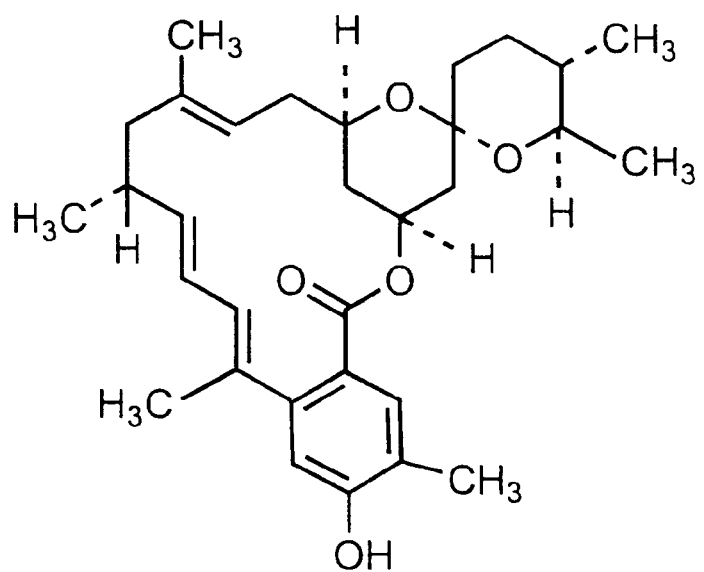
Figure 6C:
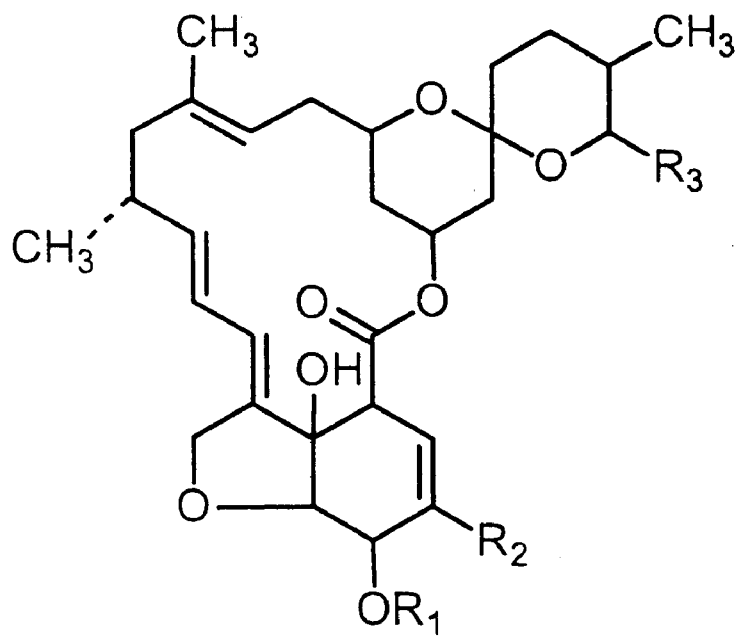
FIG. 6C shows the structures of milbemycin-type compounds (milbemycin or B-41 compounds) described in U.S. Pat. No. 3,992,551, issued Nov. 16, 1976.
Figure 7:
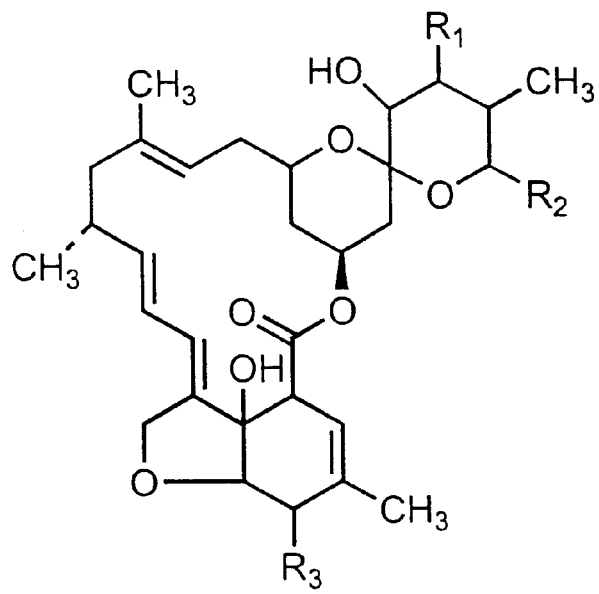
FIG. 7 shows the structures of milbemycin-type compounds described in European patent application 0 204 421 A1.
Figure 8:
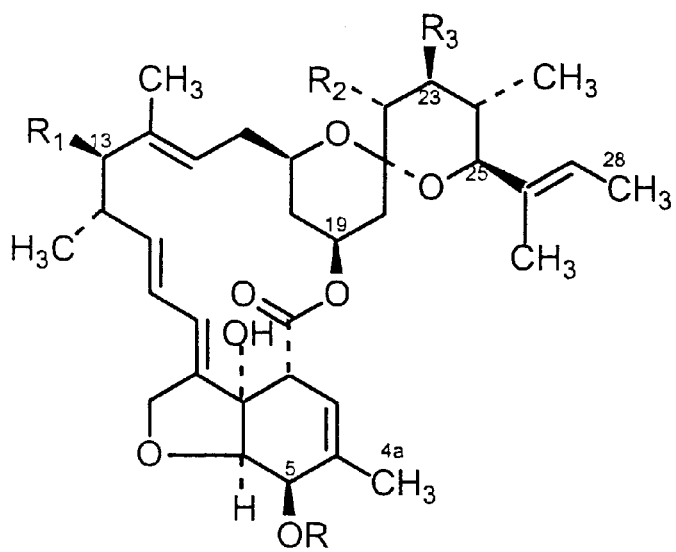
FIG. 8 shows the structures of milbemycin-type compounds described in Haxell et al., *J. Antibiotics* 45:659.
Figure 9B:
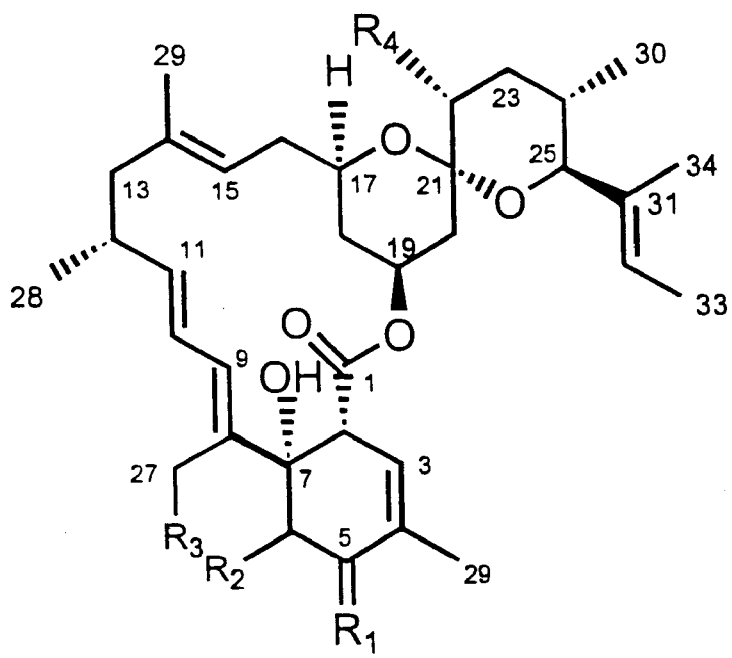
FIG. 9 shows the structures of milbemycin-type compounds (certain VM compounds) described in Baker et al., *J. Antibiotics* 49:272 (1996).
Figure 12C:
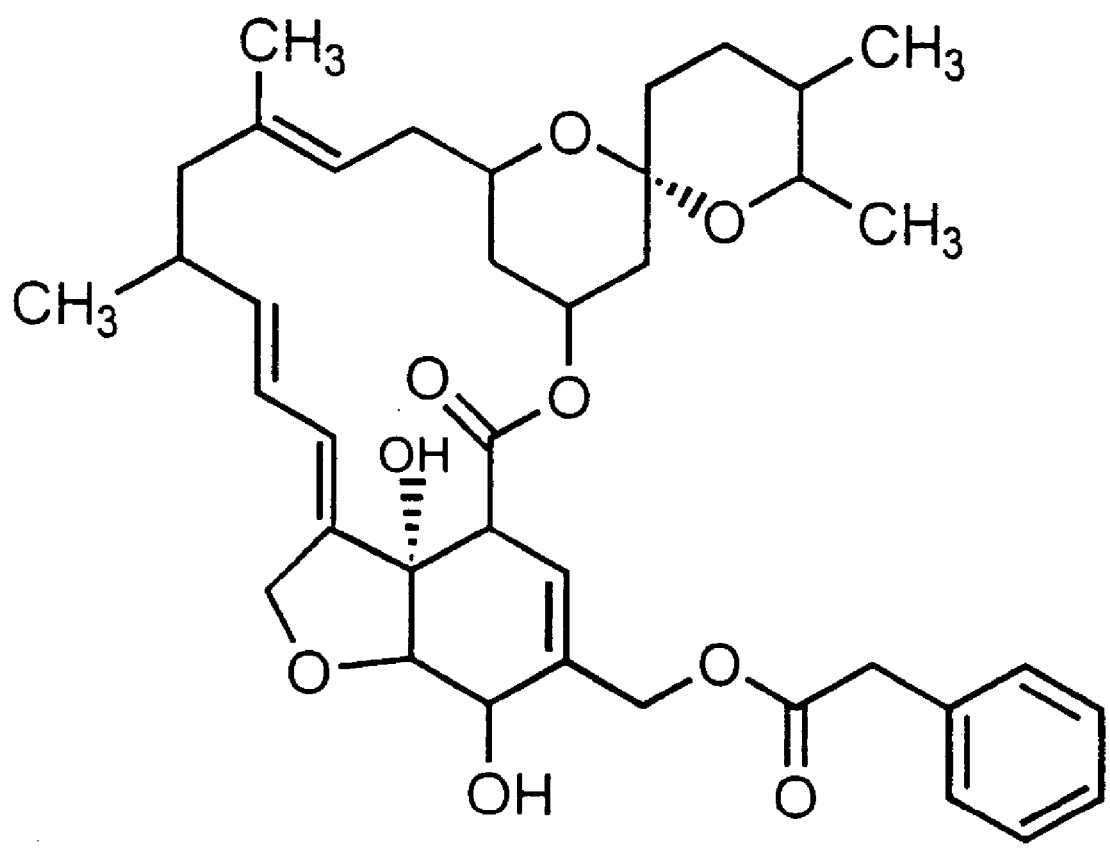
FIG. 12 shows the structures of milbemycin-type compounds described in European patent application 0 511 881 A1.
Figure 15:
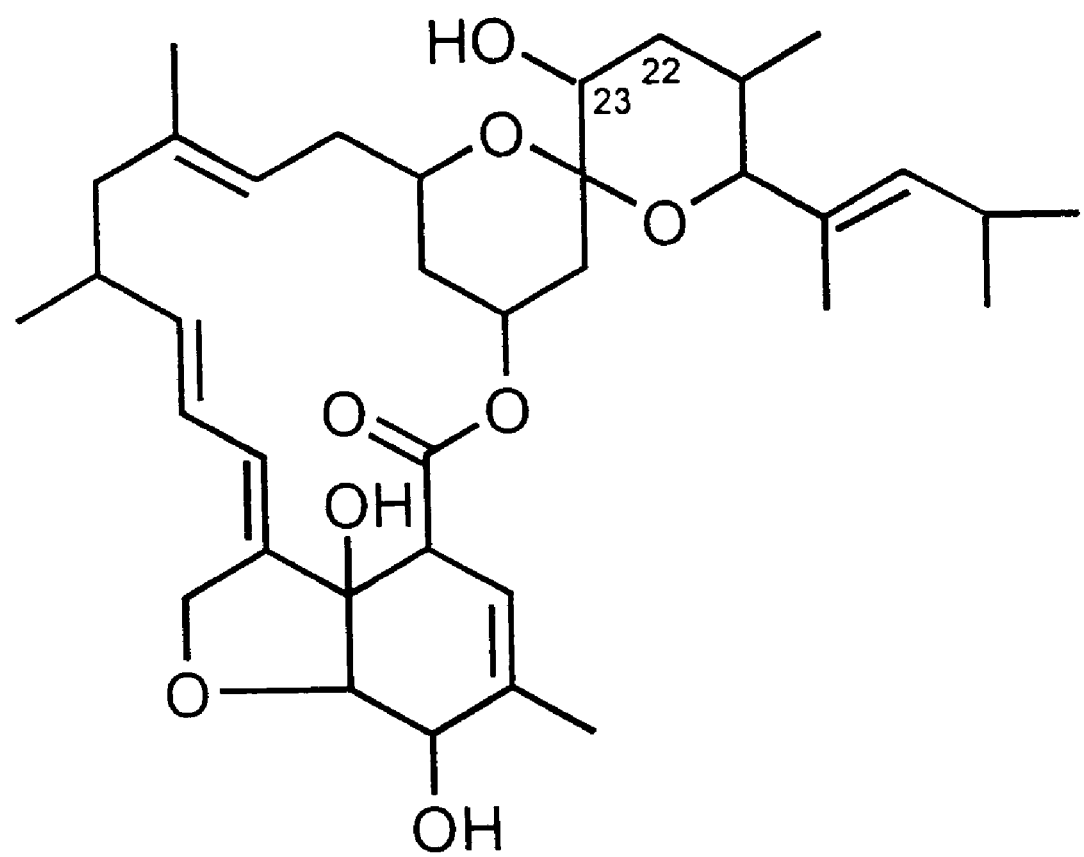
FIG. 15 shows the structures of a milbemycin-type compound (UK86,956) described in European patent application 0 410 615 A1.
Figure 16B:
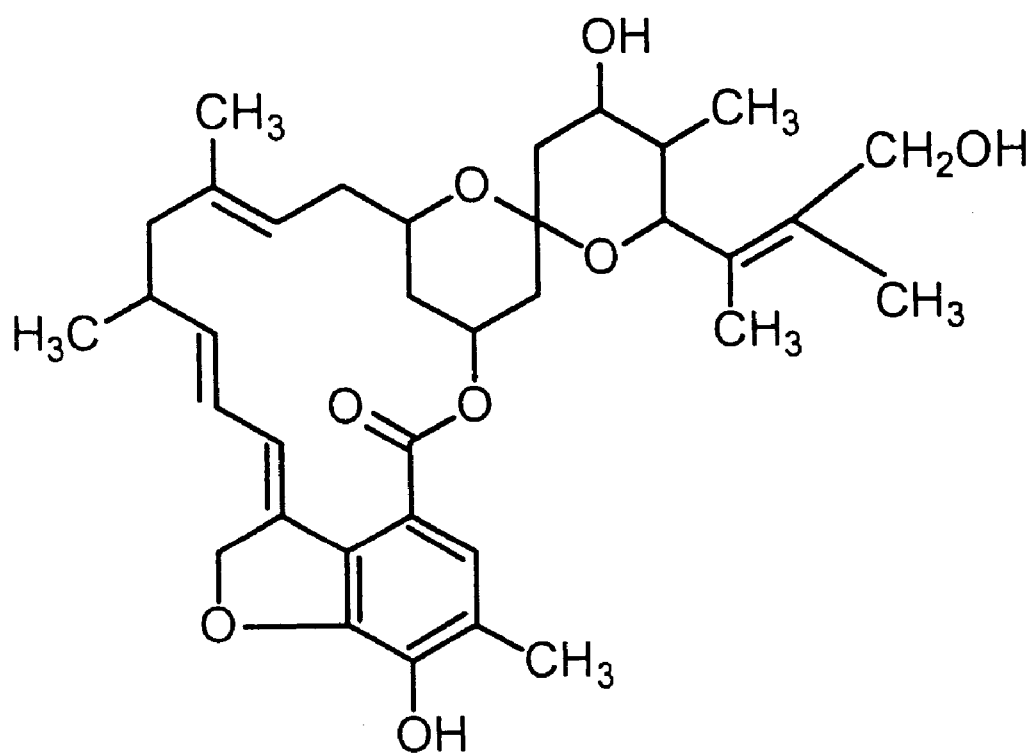
FIG. 16 shows the structures of milbemycin-type compounds (LL-F28249 compounds) described in European patent application 0 369 502 A2.
Figure 17:
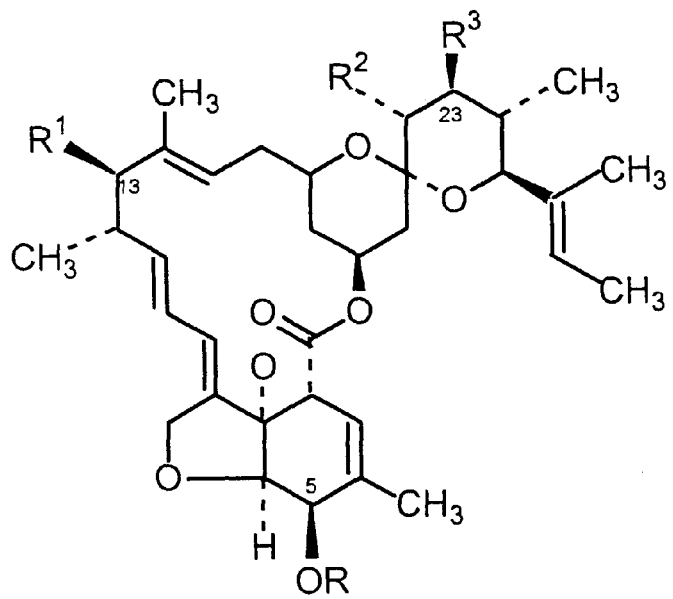
FIG. 17 shows the structures of milbemycin-type compounds (N787-182 compounds and derivatives) described in European patent application 0 334 484.
Figure 18:
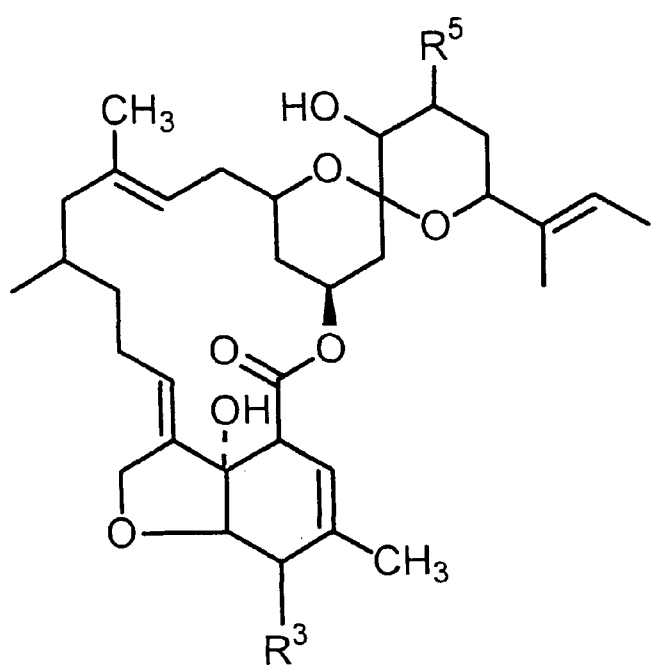
FIG. 18 shows the structures of milbemycin-type compounds (certain VM compounds) described in European patent application 0 325 462 A2.
Figure 20:
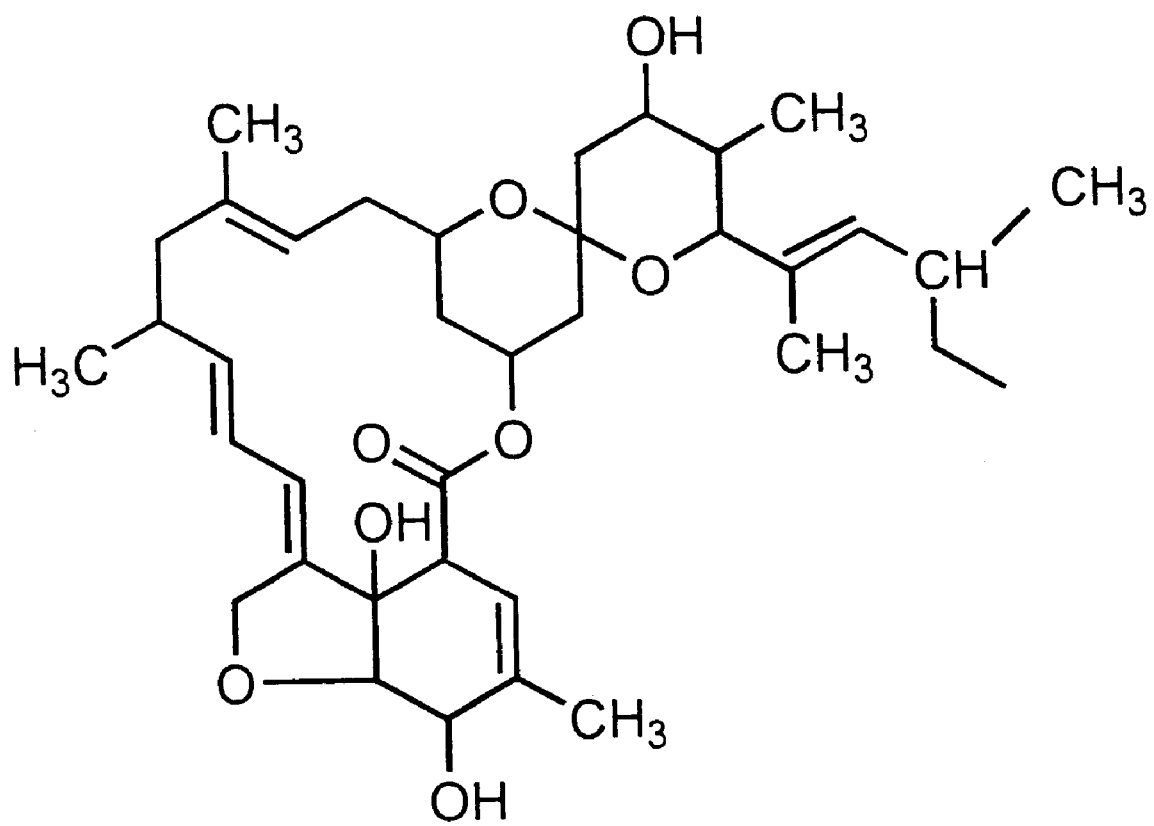

FIG. 20 shows the structures of milbemycin-type compounds described in European patent application 0 300 674 A2. The compound shown is prepared by using the same (NRRL 15773) culture used to prepare LL-F 28249α. However, the normal biosynthetic pathway is forced into a modified pathway by adding to the fermentation culture a quantity of 2-methylbutyric acid. The added 2-methylbutyric acid is incorporated intot eh molecules being prepared by the culture and produces the analogous compound with an unsaturated seven-member chain at the 25-position rather than a six-member chain.

FIG. 21 shows the structures of milbemycin-type compounds (KSB-1939 compounds) described in European patent application 0 298 423 A2. SB-1939 compounds are represented by formula I wherein R is —($CH_2$)$_n$—C(H)($CH_3$)$_2$, —($CH_2$)$_2$$CH_3$ or —CH=C($CH_3$)($CH_2$)$_m$$CH_3$, n is 0, 1 or 2, m is 0 or 1 and R' is methyl or ethyl.

Figure 22A:
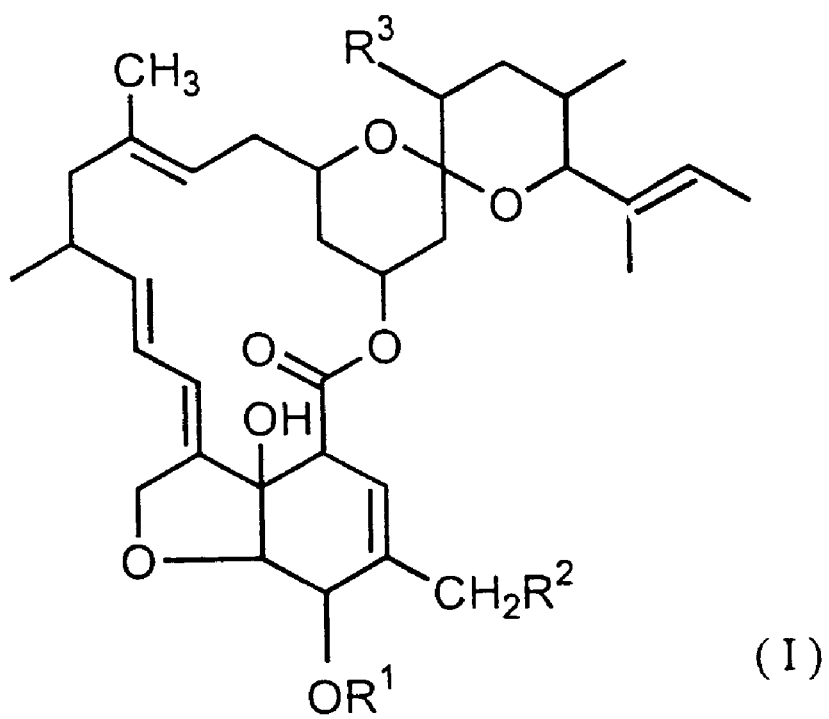

FIG. 22 shows the structures of milbemycin-type compounds described in European patent application 0 254 583 A2. In compound I, $R^1$ is hydrogen or methyl, $R^2$ is hydrogen or (E)-2-methyl-2-butenoyloxy and $R^3$ is hydrogen or hydroxy with the proviso that, when $R^3$ is hydrogen, $R^1$ and $R^2$ are both hydrogen and when $R^2$ is (E)-2-methyl-2-butenoyloxy, $R^1$ is methyl.

FIG. 23 shows the structures of milbemycin-type compounds described in European patent application 0 242 052. In Formula I, $R^1$ and $R^2$ are methyl, $R^3$ is methyl, ethyl or isopropyl and A is a ring having structure (i) or (ii) wherein $R^4$ is hydroxy or methoxy and $R^5$ is hydrogen or $R^4$ and $R^5$ taken together with the carbon atom to which they are attached are C=O or, when A is ring (ii), and $R^4$ and $R^5$ taken together are C=O, then $R^2$ may also be an aldehyde group; or $R^2$ is hydrogen and A has the structure shown in formula (iii) wherein $R^6$ is hydrogen or hydroxy; or the grouping shown as Formula (iv) is formula (v) wherein $R^7$ is hydroxy or methoxy and Z is —CHOH or C=O; or $R^1$ is hydrogen and the group shown as formula (iv) is formula (vi) wherein $R^8$ is hydroxy or methoxy, with the proviso that, when $R^2$ is methyl and $R^4$ is methoxy, then $R^3$ cannot be methyl or isopropyl and, when $R^2$ is hydroxymethyl and $R^4$ is hydroxy, then $R^3$ cannot be methyl.

Figure 24:
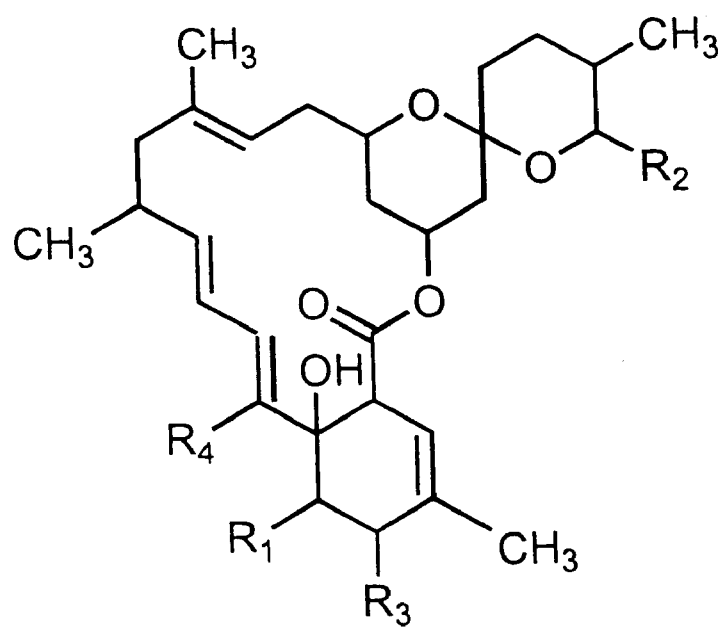

FIG. 24 shows the structures of milbemycin-type compounds described in European patent application 0 205 251. In the compound shown, $R_1$, $R_2$, $R_3$ and $R_4$ are selected as shown in the following table:

| $R_1$ | $R_2$ | $R_3$ | $R_4$ |
| --- | --- | --- | --- |
| hydroxy | methyl | methoxy | methyl |
| hydrogen | methyl | methoxy | methyl |
| hydrogen | methyl | oxo | methyl |
| hydrogen | methyl | hydroxy | methyl |
| hydrogen | methyl | methoxy | formyl |
| hydrogen | ethyl | hydroxy | methyl |

Figure 25:
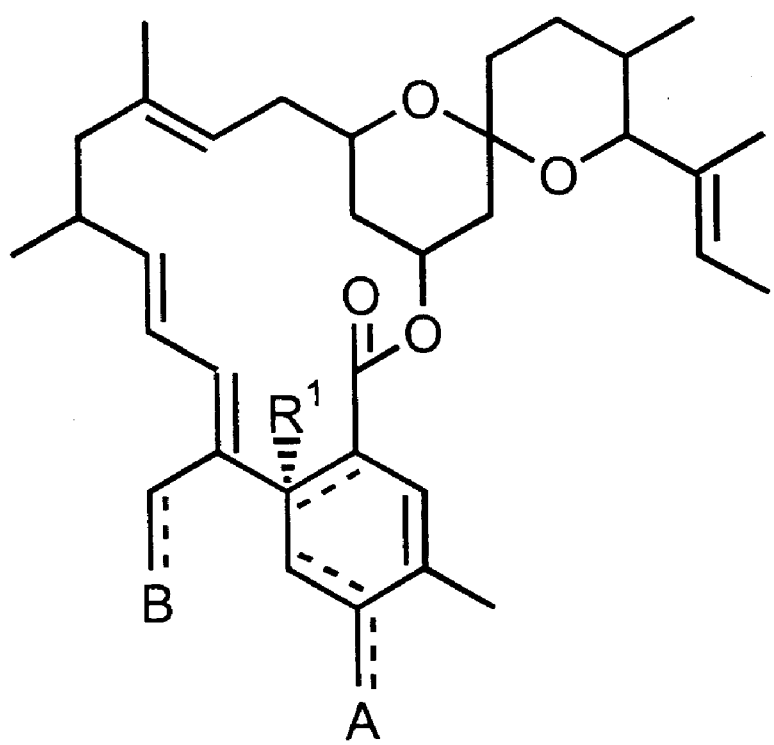

FIG. 25 shows the structures of milbemycin-type compounds described in German patent application DE 3916931 A1. In formula I, $R^1$ is hydroxy, A is =O or hydroxy, B is $NH_2$ or =O and the dotted lines represent single or double bonds.

DETAILED DESCRIPTION OF THE PREFERRED EMBODIMENTS

INTRODUCTION

The present invention concerns the inhibition of efflux pump activity by efflux pump inhibitor compounds. It further relates to the inhibitor of particular types of efflux pumps and to a particular class of compounds and to related methods for screening for other inhibitor compounds. The identification and use of efflux pump inhibitors is generally discussed in Chamberland et al., EFFLUX PUMP INHIBITORS, Internat. Patent Appl. No. PCT/US96/05469, WO96/33285. In connection with fungal efflux pumps, four MDR pumps have been demonstrated to confer resistance to fluconazole and/or other azole antifungal agents in clinical isolates of *C. albicans*. These pumps are the CDR1 and CDR2 pumps (ABC-family, Prasad et al. 1995. Molecular cloning and characterization of a novel gene from *Candida albicans*, CDR1, conferring multiple resistance to drugs and antifungals. *Curr. Genet.* 27:320–329; Fling et al., 1991, Analysis of a *Candida albicans* gene that encodes a novel mechanism for resistance to benomyl and methotrexate, *Mol. Molec. Genet.* 227:318–329; Sanglard et al., 1995; Mechanisms of resistance to azole antifungal agents in *Candida albicans* isolates from AIDS patients involve specific multidrug transporters, *Antimicrob. Agents Chemother.* 39:2378–2386; Sanglard et al. 1996. Susceptibilities of *Candida albicans* multidrug transporter mutants to various antifungal agents and other metabolic inhibitors. *Antimicrob. Agents and Chemother.* 40:2300–2305), the BEN or BenR pump (MF-family, Benyaakov et al., 1994; Fling et al., 1991, Analysis of a *Candida albicans* gene that encodes a novel mechanism for resistance to benomyl and methotrexate, *Mol. Molec. Genet.* 227:318–329; Sanglard et al., 1995; Mechanisms of resistance to azole antifungal agents in *Candida albicans* isolates from AIDS patients involve specific multidrug transporters, *Antimicrob. Agents Chemother.* 39:2378–2386), and the FLU or FLU1 pump (Sanglard et al, 1997, Cloning of *Candida albicans* genes conferring resistance to azole antifungal agents: characterization of CDR2, a new multidrug AB transporter gene, *Microbiology* 143:405–416).

The genes which encode these efflux pumps are overexpressed in several *C. albicans* isolates from AIDS patients who had failed fluconazole therapy due to fluconazole resistance. The strains which overexpressed cdr1 and cdr2 genes were cross-resistant to fluconazole, ketoconazole and itraconazole. Overexpression of benR conferred resistance to fluconazole only, but not to the other azoles. *C. albicans* strains with deletions of genes for individual pumps as well as strains with combinations of multiple deletions were constructed to further study specificity of the pumps and their role in intrinsic resistance to azole antifungals in *C. albicans*. CDR1 was shown to play a significant role in the intrinsic resistance of *C. albicans* to azoles, as deletion of the cdr1 gene rendered the strain more susceptible. CDR2 and BenR also contribute to the intrinsic resistance, however deletion of the corresponding genes affects intrinsic resistance only when cdr1 is deleted. A *C. albicans* mutant which lacks all known efflux pumps is at least 30 fold more susceptible to azoles than the parent strain. The homologs of cdr1 and benR were cloned from *C. glabrata* (cgcdr and cgben, respectively) (Sanglard et al, 1997, Cloning of *Candida albicans* genes conferring resistance to azole antifungal agents: characterization of CDR2, a new multidrug AB transporter gene, *Microbiology* 20 143:405–416)

Those skilled in the art recognize that descriptions in the literature provide identification and definition of the particular pumps referenced and also allows the identification of homologs of those pumps (e.g., the cgCDR and cgBEN homologs of the *C. albicans* pumps described above).

The existence of an active efflux pump in *Aspergillus nidulans* has also been demonstrated (Waard and van Nistelrooy. 1980. An energy-dependent efflux mechanism for fenarimol in a wild type strain and fenarimol-resistant mutants of *Aspergillus nidulans*. *Pesticide Biochem. Physiol.* 13:255–266

Thus, experimental results indicate that efflux pumps are responsible for both the acquired fluconazole resistance in clinical isolates of *C. albicans* and *C. glabrata* and the high intrinsic nonsusceptibility of different fungi to fluconazole. Involvement of the efflux pumps in resistance to azole antifungals can also explain the patterns of resistance which are seen in different resistant variants. Strains which are cross-resistant to several azole compounds overexpress CDR1-type broad-spectrum pump; strains which are resistant only to fluconazole overexpress the narrow-spectrun BenR-type pump.

It was found that compounds can be identified which inhibit the activity of fungal efflux pumps as described above. Inhibitor compounds in particular include small molecule compounds. In particular, compounds can be identified which inhibit the efflux of fluconazole. Such inhibitors are expected to i) decrease intrinsic resistance to azole antifungal agents, ii) reverse acquired resistance to azoles, and iii) broaden the spectrum of activity of fluconazole to non-susceptible fungal species.

In connection with efflux pump inhibitors, "small molecule" refers to molecules having molecular weights of less than about 3000 kDa, preferably less than about 2000 kDa, more preferably less than about 1000 kDa, and still more preferably less than about 700 kDa.

Both bacterial and mammalian MDR efflux pumps can also be inhibited by small molecules. For example, activity of P-glycoprotein, which is responsible for the resistance of tumors to anticancer drugs, can be reversed by calcium channel blockers such as verpamil and azapurine, indole alkaloids, cyclosporins and also by the immunosuppresive and antifungal agents rapamycin and FK506 (Raymond et al. 1994. Functional expression of P-glycoprotein in *Saccharomyces cerevisiae* confers cellular resistance to the immunosupressive and antifungal agent FK520. *Mol. and Cellular Biol.* 14:277–286). The use of these reversing agents in cancer therapy is currently under clinical investigation.

Screening for CDR1 CDR2 BenR, and FLU1 Efflux Pump Inhibitors

In connection with this invention, it was determined that the efflux pumps cdr1, cdr2, BenR, and Flu1 and homologs of these pumps can be used to perform useful screening for efflux pump inhibitors active on these pumps. In addition, it was found that the active efflux of fluconazole by these or other efflux pumps provides a useful screen for efflux pump inhibitors which will potentiate the antifungal activity of fluconazole and related compounds.

The screening method utilized is based on the potentiation of fluconazole activity by putative efflux pump inhibitors. The exemplary embodiment uses a *C. albicans* strain which expresses both cdr1 and BenR efflux pumps at normal levels (and/or cdr2 and/or flu1). However, other strains or species can also be used, for example, strains overexpressing one of these efflux pumps (or cdr2 or flu1). Likewise, other species can be used which express homologs of these pumps. Such screening methods thus can be used to identify compounds which increase the susceptibility of the microbe to an antimicrobial agent, for example, fluconazole, exported by one or more of these efflux pumps.

In many cases, it is helpful to provide a control, strain which does not export the antimicrobial agent or which exports the agent distinguishably less efficiently, e.g., preferably at least 2-fold less efficiently, more preferably at least 5-fold less.

In related embodiments, the screen is specifically based on export of fluconazole or a related compound which has a similar structure. The strain or species expresses at least one efflux pump which exports fluconazole. The screen therefore identifies compounds which specifically increase the susceptibility of the microbe to fluconazole or a related compound.

Screens as described above preferably also include an evaluation of the intrinsic inhibitory activity of initial screen hits or the putative efflux pump inhibitors. In addition, hits can also be further evaluated to confirm the mechanism of action. This evaluation can include determination of potentiation effect in a variety of related strains which overexpress one of the relevant efflux pumps or which does not express one of the pumps (e.g., deletion mutant or gene disruption mutant) and determination of the accumulation of the antimicrobial agent (e.g., fluconazole) in the presence of the hit compound.

An exemplary screen uses *C. albicans* (e.g., ATCC10231) grown in YPD medium (medium described in "Guide to Yeast Genetics and Molecular Biology", in *Methods in Enzymolopy*, vol. 194, pp.13, 1991,; Academic Press; Ed. C. Guthrie and G. Fink) at 30° C. Cells are grown in the presence and absence of 0.5 µg/ml fluconazole and the presence and absence of 5–10 µg/ml test compound or a natural products extract. Test and control cultures are inoculated with log-phase cells to provide approximately $10^3$ CFU/ml. Cultures are incubated at 30° C. for 20–22 hrs. Cell concentration is determined by taking the OD600.

CDR1 Efflux Pump Inhibitors

Screening as described above using a variety of natural products extracts and synthetic compounds produced a number of hits, thereby identifying putative inhibitors of an efflux pump in *C. albicans*. Follow-up evaluation demonstrated that a compound isolated from an actinomycete fermentation inhibited the CDR1 efflux pump, but did not appreciably inhibit the BenR pump. As further described below, this compound was determined to be a milbemycin, and was found to be the compound described as milbemycin $\beta_1$ (or A1) in Takiguchi et al, *J. Antibiotics,* 33:1120–1127, 1980; Okazaki et al, *J. Antibiotics,* 36:438–441, 1983; U.S. Pat. No. 3,950,360, 1976; Acki et al., U.S. Pat. No. 3,992, 551.

Milbemycins and milbemycin-type compounds are families of compounds with closely related chemical structures isolated from the fermentation of a number of different streptomycetes strains. Milbemycins and milbemycin-type compounds, and the structurally related avermectins, are potent insecticidal and antiparasitic agents. Extensive semi-synthetic chemical modifications have been conducted on both the milbemycins and the avermectins and resulted in the development of a number of commercially available antiparasitic agents for use in plant crop protection, animal husbandry, animal health care and human health care (H. G. Davies and R. H. Green, 1991, *Chem. Soc. Rev.* 20: 211–269, 271–339 and references therein).

Obtaining Milbemycin Compounds

As described above, a variety of different milbemycins and milbemycin analogs and derivatives have been identified and described. Therefore, one skilled in the art can readily obtain milbemycins for use in this invention or for the creation of compounds having chemical modifications for use in this invention using the sources and methods disclosed in references cited in connection with identified milbemycins and related compounds. For example, milbemycins and other milbemycin-type compounds can be obtained by the fermentation of the deposited Streptomyces strains reported in those references, including (strains identified by deposit number) Streptomyces NRRL 5739 (B-41 compounds), *Streptomyces cyaneogriseus* subsp. *noncyanogenus* NRRL 15773 (LL-F28249 compounds, preferably compounds α-µ), *Streptomyces hygroscopius* ATCC 53718 (N 787-182 compounds), Streptomyces ATCC 53110, *Streptomyces thermoarchaensis* or *cyaneogriseus* NCIB 12015, 12111, 12112, 12113, 12114, 12212, 12334 (S541 compounds), Streptomyces NCIB 12310 and 12509 (VM compounds), Streptomyces FERM BP 1901 (KSB-1939 compounds), *Streptomyces griseochromogenes* ATCC 53928 (UK-86,956 compounds), and *Streptomyces hygroscopius ATCC* 55144, 55145, and 55146. Milbemycin-type compounds can also be obtained from other organisms as known to those skilled in the art.

Confirmation of activity can, if desired, be carried out using any of a large variety of strains, e.g., *C. albicans* strains, expressing an efflux pump which exports a relevant second compound, such as an antifungal agent (e.g., fluconazole). Suitable strains will generally be those having essentially normal susceptibility to the antimicrobial agent in question. However, strains having reduced susceptibility can also be used, especially if the strain is confirmed to overexpress an efflux pump which exports the antimicrobial, agent in question. In addition, strains which have increased susceptibility to the agent or which have been shown to lack or underexpress such an efflux pump can be used for further evaluation of putative efflux pump inhibitors. Examples of the use of such strains are provided in the Examples below. One skilled in the art can readily isolate or create similar strains by conventional selection using the antimicrobial (e.g., antifungal) agent followed by confirmation of efflux pump overexpression or by creating strains lacking, underexpressing, or overexpressing a particular efflux pump by inactivating a chromosomal efflux pump gene and/or by inserting one or more copies of the coding regions for such a pump under altered regulation and/or in multiple copies (e.g., on a plasmid(s) or by genomic insertion).

Milbemycin Derivatives

Derivatives of naturally-occurring milbemycins can be obtained using chemical modification, microbial transformation, directed biosynthesis, and chemical synthesis methods as known to those skilled in the art. Descriptions of some examples of such modifications and syntheses are provided in references cited herein in connection with milbemycin analogs and derivatives which have already been produced. Such derivative compounds which retain or have gained efflux pump inhibiting activity are within the present invention.

Inhibiting Growth of Cells and Therapeutic Treatment

The ability of milbemycin-type compounds, such as milbemycin $\beta_1$, to inhibit the activity of efflux pumps such as the fungal CDR1 pump or the mammalian P-glycoprotein allows these compounds to be used for therapeutic purposes and to be prepared in pharmaceutical compositions as well as to be used in other applications where inhibition of cell growth is desired. In the case of these efflux pumps, the milbemycin-type compound is administered in combination with another compound which is normally exported by the efflux pump. In the absence of an efflux pump inhibitor, the intracellular concentration of the second compound, typically an antimicrobial agent or an anti-cancer agent, is maintained at a low level by the efflux pump. Often this level is such that the ability of the second compound to inhibit the growth of the cell is limited or absent. In therapeutic uses, this can result in the inability to use that compound. The presence of the milbemycin-type compound efflux pump inhibitor reduces the export of the second compound, allowing it to accumulate within the cell to an effective level. Thus, the milbemycin-type compound enables the use of the second compound with microbial strains or cells which would otherwise by resistant, or alternatively allows the use of the second compound at lower concentrations, thereby reducing potential side effects.

Pharmaceutical Compositions and Modes of Administration

The particular compound that is an efflux pump inhibitor can be administered to a patient either by itself, or in combination with an antimicrobial agent, or in pharmaceutical compositions where it is mixed with suitable carriers or excipient(s). A combination of an efflux pump inhibitor with an antimicrobial agent can be of at least two different types. In one, a quantity of an efflux pump inhibitor is combined with a quantity of an antimicrobial agent in a mixture, e.g., in a solution or powder mixture. In such mixtures, the relative quantities of the inhibitor and the antimicrobial agent may be varied as appropriate for the specific combination and expected treatment. In a second type of combination an inhibitor and an antimicrobial agent can be covalently linked in such manner that the linked molecule can be cleaved within the cell. However, the term "in combination" can also refer to other possibilities, including serial administration of an inhibitor and another antimicrobial agent. In addition, an efflux pump inhibitor and/or another antimicrobial agent may be administered in pro-drug forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. In particular for internal use, the dosage of such compounds lies preferably within a range of circulating concentrations that include the $ED_{50}$ with little or no toxicity. The dosage may vary within this range depending upon the dosage form employed and the route of administration utilized. It is preferable that the therapeutic serum concentration of an efflux pump inhibitor should be in the range of 0.1–100 $\mu$g/ml.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture Such information can be used to more accurately determine useful doses in humans. Levels in plasma may be measured, for example, by HPLC.

In particular preferred embodiments, the efflux inhibitor in a pharmaceutical composition has a structure as shown by the generic structures described above.

The exact formulation, route of administration and dosage can be chosen by the individual physician in view of the patient's condition. (See e.g. Fing1 et al., in THE PHARMACOLOGICAL BASIS OF THERAPEUTICS, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific infection being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art, into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLES

In the subsequent section, exemplification of the fungal mode-of-action of and milbemycin-related structures is provided. The fungal efflux inhibitors described in this invention are either described specifically in the text or listed as compound numbers. These compound numbers are cross-referenced below.

Fungal Efflux Pump Inhibitors Described in Tables 1–15

| Compound | Name |
|---|---|
| 1 | Ivermectin $B_{1a}$ |
| 2 | Milbemycin oxime |
| 3 | Milbemycin $\alpha_1$ |
| 4 | Milbemycin $\alpha_2$ |
| 5 | Milbemycin $\beta_1$ aldehyde |
| 6 | Milbemycin $\beta_1$ |
| 7 | Milbemycin $\alpha_3$ |
| 8 | Milbemycin $\alpha_5$ |
| 9 | Milbemycin $\alpha_6$ |
| 10 | Milbemycin $\alpha_7$ |
| 11 | Milbemycin $\alpha_9$ |
| 12 | Milbemycin D |
| 13 | Milbemycin $\beta_3$ |
| 14 | Avermectin $\beta_{2a}$ aglycone |
| 15 | LL-F2849$\alpha$ (nemedectin$_\alpha$) |
| 16 | LL-F2849$\lambda$ (nemedectin$_\lambda$) |
| 17 | LL-F2849$\zeta$ (nemedectin$_\zeta$) |
| 18 | LL-F2849$\alpha$ oxime |
| 19 | 8-Methyl-5,6-dihydroxymilbemycin $\beta_1$ |
| 20 | 4a-O-isobutyryl milbemycin $\alpha_1$ |
| 21 | 4a-O-(2-ethyl)butyryl milbemycin $\alpha_1$ |
| 22 | 5-Keto-8-deoxymilbemycin $\beta_1$ |
| 23 | Avermectin $B_{2a}$ monoglycoside |
| 24 | 8-Methyl-8-deoxymilbemycin $\beta_1$ |
| 25 | 4a-O-phenylacetyl milbemycin $\alpha_1$ |

Example 1

Potentiation of Fluconazole Against *S. cerevisiae* Overexpressing Candida Efflux Pumps by Milbemycin $\beta_1$.

Milbemycin $\beta_1$ used for the tests described herein was isolated from fermentation of an unidentified actinomycetes. Its physical-chemical and NMR spectral characteristics showed that its chemical structure is identical to milbemycin $\beta_1$ which was produced by FERM P-1438 (Fermentation Research Institute, Agency of Industrial Science and Technology, Ibaragi, Japan) and which is described in (Takiguchi et al., *J. Antibiotics,* 33:1120–1127, 1980; Mishimi et al., *J. Antibiotics,* 36:438–441, 1983). Milbemycin $\beta_1$ can be obtained as described in those references, which are hereby incorporated by reference.

The MIC of fluconazole against various strains of *S. cerevisiae* in the presence of milbemycin $\beta_1$ (1.25 µg/ml) was determined using broth dilution assay in microtiter plates, is shown in Table 1 below.

TABLE 1

Effect of milbemycin $\beta_1$ (Mb) (1.25 µg/ml) on the susceptibility of *S. cerevisiae* strains to fluconazole (Flu).

| | | | MIC (mg/ml) | | |
|---|---|---|---|---|---|
| Strain | Efflux Pump Introduced | Pump Family | Mb | Flu | Flu + Mb (1.25 µg/ml) |
| YEM-3 | — | — | 8 | 0.25 | 0.25 |
| YEM-1 | CDR1 | ABC-transporter | 8 | 128 | 0.25 |
| YEM-37 | CDR2 | ABC-transporter | 8 | 2 | 0.25 |
| YEM-39 | CgCDR | ABC-transporter | 8 | 32 | 1 |
| YEM-2 | BEN | MF | 8 | 128 | 128 |
| YEM-40 | CgCDR | MF | 8 | 16 | 16 |
| YEM-38 | FLU1 | MF | 8 | 4 | 4 |

*S. cerevisiae* YEM-3 is the genetic background to which plasmid containing genes coding efflux pumps of *C. albicans* and *C. glabrata* (prefixed with Cg) were introduced to give the respective strains in Table 1. Milbemycin $\beta_1$ potentiates the activity of fluconazole against *S. cerevisiae* strains carrying the ABC-transporter class of efflux pumps. Milbemycin $\beta_1$ is an inhibitor of efflux pumps of the ABC-transporter family.

Example 2
Potentiation of Fluconazole Against Pump Deletion Mutants of *Candida albicans* by Milbemycin $\beta_1$ The MIC of fluconazole against various strains of *C. albicans*, in the presence of milbemycin $\beta_1$ (2.5 µg/ml), was determined using broth dilution assay in microtiter plates is shown in Table 2 below.

TABLE 2

Effect of milbemycin $\beta_1$ (Mb) (2.5 µg/ml) on the susceptibility of *C. albicans* strains to fluconazole (Flu).

| | | MIC (µg/ml) | | |
|---|---|---|---|---|
| Strain | Efflux pump deleted | Mb | Flu | Flu + Mb (2.5 µg/ml) |
| YEM-30 | — | 16 | 0.5 | 0.125 |
| YEM-20 | CDR1 | 16 | 0.125 | 0.125 |
| YEM-24 | CDR1, CDR2 | 16 | 0.125 | 0.125 |
| YEM-21 | BEN | 16 | 0.25 | 0.03 |
| YEM-29 | BEN, FLU1 | 16 | 0.25 | 0.03 |
| YEM-27 | CDR1, CDR2, BEN, FLU1 | 16 | 0.03 | 0.03 |

*C. albicans* YEM-30 (CAF2-1, W. A. Fonzi and M. Y. Irwin. Isogenic strain construction and gene mapping in *Candida albicans*. Genetics 134:717–728 1992) is a strain with wild-type level of fluconazole susceptibility, from which the genes coding the various efflux pumps were disrupted to give the respective pump deletion mutant strains in Table 2. The potentiation effect of milbemycin $\beta_1$ against the wild type strain was not changed when CDR1 or CDR2 pumps, both of the ABC-transporter family, were disrupted. The potentiation effect of milbemycin $\beta_1$ against strains where the BEN and FLU1 pumps, both of the major facilitator family, were disrupted was enhanced. Milbemycin is an effective inhibitor of the ABC-transporter family of efflux pumps, but has minimal effect on the Major facilitator family of efflux pumps. No effect of milbemycin $\beta_1$ was observed against a strain which lacked all identified efflux pumps, YEM-27.

Example 3
Potentiation of Fluconazole Against Fluconazole-resistant Isolates of *C. albicans* by Milbemycin $\beta_1$ MIC of fluconazole against various strains of *C. albicans*, in the presence of milbemycin $\beta_1$ (2.5 µg/ml), was determined using broth dilution assay in microtiter plates is shown in Table 3 below.

TABLE 3

Effect of milbemycin $\beta_1$ (Mb) (2.5 µg/ml) on the susceptibility of clinical isolates of *C. albicans* to fluconazole (Flu).

| | | MIC (µg/ml) | | |
|---|---|---|---|---|
| Strain | Efflux pump expressed | Mb | Flu | Flu + Mb (2.5 µg/ml) |
| YEM-10 | Low level CDR1 expressor | 16 | 0.25 | 0.125 |
| YEM-14 | Low level CDR1 expressor | 16 | 0.125 | 0.125 |
| YEM-12 | Low level CDR1 expressor | 32 | 2 | 0.25 |
| YEM-11 | BEN overexpressor | 16 | 32 | 32 |
| YEM-13 | BEN overexpressor | 32 | 32 | 32 |
| YEM-15 | CDR1 and CDR2 overexpressor | 16 | 128 | 1 |
| YEM-5 | CDR1 and CDR2 overexpressor | ND | >128 | 8 |

Milbemycin $\beta_1$ potentiated the activity of fluconazole against clinical isolates of *C. albicans* with resistance due primarily to the overexpression of $CDR_1$ and CDR2 efflux pumps, both of the ABC-transporter pump family.

Example 4
Potentiation of Fluconazole Against Fluconazole-resistant Isolates of *C. glabrata* by Milbemycin $\beta_1$ The MIC of fluconazole against various strains of *C. glabrata*, in the presence of various concentrations of milbemycin $\beta_1$, was determined using broth dilution assay in microtiter plates is shown in table 4 below.

TABLE 4

Effect of various concentrations of milbemycin $\beta_1$ (Mb) on the susceptibility of clinical isolates of *C. glabrata* to fluconazole (Flu).

| | | | Fluconazole MIC[a] (µg/ml) with different conc. of milbemycin $\beta_1$ (µg/ml) | | | | |
|---|---|---|---|---|---|---|---|
| Strain | Efflux pump expressed | MB (µg/ml) | 0 | 1.25 | 2.5 | 5 | 10 |
| YEM-16 | Low level CgBEN and CgCDR expression | >64 | 16 | 2 | 1 | 2 | 2 |
| YEM-18 | Low level CgBEN and CgCDR expression | >64 | 8 | 2 | 2 | 2 | 2 |
| YEM-17 | CgCDR overexpressor | >64 | 64 | 8 | 4 | 2 | 2 |
| YEM-19 | CgCDR overexpression (higher than YEM-17) | >64 | 128 | 32 | 8 | 2 | 2 |

[a]NCCLS susceptibility breakpoint for fluconazole is 8 µg/ml.

Milbemycin $\beta_1$ potentiated the activity of fluconazole against isolates of *C. glabrata* and brought the susceptibility level to four-fold below the NCCLS breakpoint.

Example 5

Inhibition of P-glycoprotein by Milbemycin $\beta_1$

The inhibitory effect of milbemycin $\beta_1$ against the mammalian P-glycoprotein multi-drug resistant pump was determined following the procedure described by Tsuruo et al (Cancer Res., 1981. 41:1967–1972) with slight modification. The cytotoxicity of antitumor agent, adriamycin, against adriamycin sensitive P388 cell line (mouse leukemia) and its adriamycin resistant subline line (P388/ADM) was measured in the presence of various concentrations of milbemycin $\beta_1$. Verapamil, a known p-glycoprotein inhibitor was used as a positive control of the test. The assay is performed in serum-free media containing 20 μM of 2-mercaptoethanol. Chemosensitivity to adriamycin was determined calorimetrically based on the reduction of MTT (3-[4,5-dimethylthiazol-2-yl]-2,5-diphenyltetrazolium bromide) into blue formazan. Cell lines are incubated at 37° C. for 72 hr. with or without verapamil or different concentrations of milbemycin $\beta_1$. The test results, expressed as a ratio of $TC_{50}$ in P388 vs. P388/ADM are shown in Table 5 below.

TABLE 5

Inhibition of the P-glycoprotein multidrug resistant pump by milbemycin $\beta_1$.

| Compounds | Conc. in P-Gly assay (μg/ml) | Adriamycin $TC_{50}$(ng/ml) P388 | P388/ ADM | Ratio [P388/A]/ [P388] | $TC_{50}$ in K-562 (μM) |
|---|---|---|---|---|---|
| None | | 9 | 2954 | 337 | |
| Verapamil | 1 | 7 | 125 | 17 | 38 |
| Milbemycin* | 3.125 | 11 | 51 | 5 | 8** |
| | 2 | 12 | 50 | 4 | |
| | 1 | 9 | 215 | 23 | |
| | 0.5 | 11 | 369 | 32 | |
| | 0.25 | 9 | 660 | 75 | |
| | 0.125 | 8 | 848 | 103 | |
| | 0.06 | 9 | 1955 | 220 | |

*A concentration of 4 μg/ml of milbemycin $\beta_1$ is toxic and destroys the monolayers of both P388 and P388/ADM cell lines
**The $TC_{50}$ of Milbemycin for K-562 cell is 8 μM or 4 μg/ml Milbemycin $\beta_1$ is an inhibitor of the mammalian p-glycoprotein multi-drug resistant pump with potency similar to that of verapamil.

Example 6

Potentiation of Fluconazole Against Clinical Isolates of Candida by Milbemycin Oxime "Milbemycin oxime" is a mixture of the oxime derivative of 5-dehydro-5-deoxymilbemycin, in the ratio of ca. 80% milbemycin $A_4$ and 20% milbemycin $A_3$. The chemical structures of milbemycin $A_4$ and milbemycin $A_3$ are as described in Takiguchi et al., 1980, J. Antibiotics 33:1120–1137.

The MIC of fluconazole against various species of Candida, in the presence of milbemycin oxime (2.5 μg/ml), was determined using broth dilution assay in microtiter plates is shown in Table 6 below.

TABLE 6

Effect of milbemycin oxime (MbOxm) (2.5 μg/ml) on the susceptibility of clinical isolates of Candida to fluconazole (Flu)

| | | | MIC (μg/ml) | |
|---|---|---|---|---|
| Strain | Organism | Efflux Pump Expressed | Flu | Flu + McOxm (2.5 μg/ml) |
| YEM-15 | C. albicans | CDR1 & CDR2 overexpressor | 128 | 0.25 |
| YEM-19 | C. glabrata | CgCDR overexpressor | >128 | 128 |
| YEM-52 (ATCC 90878) | C. krusei | wild type | 64 | 2 |

As shown in the above table, milbemycin oxime effectively potentiates the activity of fluconazole against clinical isolates of C. albicans and C. krusei.

Example 7

Potentiation of Fluconazole Against Candida Species by Milbemycin $\beta_1$ and Milbemycin Oxime The minimal concentration of milbemycin $\beta_1$ or milbemycin oxime required to decrease the MIC of fluconazole against various species of Candida by 16-fold was determined using broth dilution assay in microtiter plates. The results are shown in Table 7 below.

TABLE 7

Minimal concentration of milbemycin and milbemycin oxime required to reduce the MIC of fluconazole by sixteen-fold.

| | | | Minimal Concentration (μg/ml) | |
|---|---|---|---|---|
| Strain | Organism | Efflux Pump Expressed | Milbemycin | Milbemycin oxime |
| YEM-13 | C. albicans | BEN | 80 | 80 |
| YEM-15 | C. albicans | CDR1 & CDR2 overexpressor | <0.07 | <0.07 |
| YEM-19 | C. glabrata | CgCDR overexpressor | 2.5 | >80 |
| YEM-52 (ATCC 90878) | C. krusei | wild type | 1.25 | 1.25 |

Both milbemycin $\beta_1$ and milbemycin oxime are effective in potentiating the activity of fluconazole against C. albicans which overexpresses the ABC transporter family of pumps (CDR1 and CDR2) and a wild type C. krusei. Milbemycin $\beta_1$ is effective in potentiating the activity of fluconazole against C. glabrata, while milbemycin oxime is not. Neither milbemycin $\beta_1$ nor milbemycin oxime are effective in potentiating the activity of fluconzaole against the C. albicans strain carrying the BEN pump (major facilitator pump family).

Example 8

Potentiation of Several Azoles and Terbinafine Against Clinical Isolates of Candida by Milbemycin $\alpha_9$ The MICs of several azoles (e.g., fluconazole, itraconazole, ketoconazole), and terbinafine against three species of Candida in the presence of various concentrations of milbemycin $\alpha_9$ were determined using standard broth dilution checkerboard assay. The minimal concentration of milbemycin $\alpha_9$ required to achieve maximum reduction in MICs of various antifungal agents was determined (FEPI$_{max}$). The MIC Reduction Factor (or fold-decrease) in the presence of milbemycin α$_9$ at the FEPI$_{max}$ (μg/ml) concentration was calculated.

TABLE 8

Effect of Milbemycin α$_9$ on potentiation of azoles and terbinafine against clinical isolates of Candida species

| Strain | YEM-15 | YEM-17 | YEM-71 |
|---|---|---|---|
| Organism | C. albicans | C. glabrata | C. krusei |
| Efflux Pump Expressed | CDR1 & CDR2 overexpressor | CgCDR overexpressor | ND* |
| Milbemycin α$_9$ MIC (μg/ml) | >64 | >64 | >64 |
| Fluconazole | | | |
| MIC (μg/ml) | 128 | 128 | 128 |
| FEPI$_{max}$ (μg/ml) | 16 | 8 | 1 |
| MIC in the presence of FEPI$_{max}$ (μg/ml) | 2 | 4 | 8 |
| MIC Reduction Factor | 64 | 32 | 16 |
| Itraconazole | | | |
| MIC (μg/ml) | 0.5 | 128 | 0.5 |
| FEPI$_{max}$ (μg/ml) | 1 | 4 | 0.25 |
| MIC in the presence of FEPI$_{max}$ (μg/ml) | 0.06 | 0.125 | 0.008 |
| MIC Reduction Factor | 8 | 1024 | 64 |
| Ketoconazole | | | |
| MIC (μg/ml) | 1 | 2 | 2 |
| FEPI$_{max}$ (μg/ml) | 4 | 16 | 2 |
| MIC in the presence of FEPI$_{max}$ (μg/ml) | 0.015 | 0.06 | 0.015 |
| MIC Reduction Factor | 64 | 32 | 128 |
| Terbinafine | | | |
| MIC (μg/ml) | 128 | 128 | 128 |
| FEPI$_{max}$ (μg/ml) | 4 | 4 | 0.008 |
| MIC in the presence of FEPI$_{max}$ (μg/ml) | 0.125 | 4 | 2 |
| MIC Reduction Factor | 1024 | 32 | 64 |

*ND-not determined

As shown in Table 8, milbemycin α$_9$ potentiates activity of various azoles and terbinafine against C. albicans and C. glabrata, which overexpress ABC-type efflux pumps (CDR1/CDR2 or CgCDR) and against C. krusei (efflux pump not identified). The potency of milbemycin ag as expressed by FEPI$_{max}$ varied depending on the antifungal agent and Candida species.

Example 9

Potentiation of Fluconazole and Terbinafine Against S. cerevisiae Overexpressing Candida Efflux Pumps by Milbemycin α$_9$ MICs of fluconazole and terbinafine against recombinant strains of S. cerevisiae overexpressing various Candida efflux pumps were determined in the presence of various concentrations of milbemycin α$_9$ using standard two-fold broth dilution checkerboard assay. All recombinant strains used in this study were constructed by introducing vector plasmids with genes encoding various Candida efflux pumps into the strain that lacks efflux pump. Thus, increased resistance to antifungal agents in the recombinant strains versus the parent strain is due to efflux pump activity. The minimal concentration of milbemycin α$_9$ required to achieve maximum reduction in MIC is reported as FEPI$_{max}$. The degree of pump inhibition (DI) in the presence of milbemycin α$_9$ at concentration corresponding to FEPI$_{max}$ was calculated as follows:

$$DI\ (\%) = \frac{(\log_2 MIC_{YEM-X} - \log_2 MIC_{YEM-X+FEPImax})}{(\log_2 MIC_{YEM-X} - \log_2 MIC_{YEM-3})} \times 100$$

where the terms are:

| | |
|---|---|
| MIC$_{YEM-X}$ | MIC for the corresponding strain |
| FEPI$_{max}$ | minimal conc. required for maximum reduction of MIC |
| MIC$_{YEM-X+FEPImax}$ | MIC in presence of milbemycin α$_9$ at FEPI$_{max}$ · conc. |
| MIC$_{YEM-3}$ | MIC for the parent strain (no pump, corresponds to the maximal possible inhibition). |

TABLE 9

Potentiation profile of milbemycin α$_9$ with fluconazole and terbinafine against S. cerevisiae overexpressing Candida efflux pumps

| Strain | YEM-1 | YEM-37 | YEM-39 |
|---|---|---|---|
| Efflux Pump Expressed | CDR1 (C. albicans) | CDR2 (C. albicans) | CgCDR (C. glabrata) |
| Milbemycin α$_9$ MIC (μg/ml) | >64 | >64 | >64 |
| Fluconazole | | | |
| MIC (μg/ml) | 128 | 4 | 64 |
| FEPI$_{max}$ (μg/ml) | 2 | 1 | 2 |
| MIC in the presence of FEPI$_{max}$ (μg/ml) | 0.5 | 0.5 | 4 |
| MIC Reduction Factor | 256 | 8 | 16 |
| Pump inhibition (%) | 100 | 100 | 60 |
| Terbinafine | | | |
| MIC (μg/ml) | 128 | 2 | 4 |
| FEPI$_{max}$ (μg/ml) | 0.5 | 4 | 2 |
| MIC in the presence of FEPI$_{max}$ (μg/ml) | 0.5 | 0.5 | 1 |
| Pump inhibition (%) | 100 | 100 | 66 |

As shown in Table 9, milbemycin α$_9$ inhibits efflux pumps from ABC-family of transporters. It completely inhibits CDR1 and CDR2 pump from C. albicans and significantly inhibits CgCDR efflux pump from C. glabrata (60–65%).

Example 10

Comparative Activity of Various Milbemycins Against Efflux Pumps from Candida Species Inhibition profile of various milbemycins was determined in recombinant strain of S. cerevisiae overexpressing Candida efflux pumps. The MICs of milbemycins against these strains were determined in the presence of fixed concentrations of fluconazole using standard two-fold broth dilution assay. Fluconazole was added at concentrations that were expected if the corresponding efflux pump was inhibited 50% (FLU$_{half}$). Because of two-fold dilution scheme in MIC determination, this concentration was calculated as follows:

$$FLU_{half} = (MIC_{YEM-X} \times MIC_{YEM-3})^{1/2}$$

where the values are:

| | |
|---|---|
| $MIC_{YEM-X}$ | MIC for the corresponding strain |
| $MIC_{YEM-3}$ | MIC for the parent strain (no pump, or maximal possible inhibition) to fluconazole is 0.5 µg/ml. |

The method allowed determination of concentrations of various milbemycins needed to reduce activity of efflux pumps by 50%. The results are presented in Table 10.

TABLE 10

Profile of Various Milbemycins as Inhibitors of Fungal Efflux Pumps

| STRAIN<br>Pump<br>Origin<br>of pump<br>Flucona-<br>zole MIC<br>COM-<br>POUND | YEM-1<br>pCDRI<br>(ABC)<br>C.<br>albicans<br>128<br>$FEPI_{half}$<br>(5.6)* | YEM-37<br>pCDR2<br>(ABC)<br>C.<br>albicans<br>4<br>$FEPI_{half}$<br>(1)* | YEM-39<br>pCgCDR<br>(ABC)<br>C.<br>glabrata<br>64<br>$FEPI_{half}$<br>(4)* | YEM-2<br>pBEN<br>(MF)<br>C.<br>albicans<br>128<br>$FEPI_{half}$<br>(5.6)* | YEM-38<br>pFLU<br>(MF)<br>C.<br>albicans<br>16<br>$FEPI_{half}$<br>(2)* | YEM-40<br>pCgBEN<br>(MF)<br>C.<br>glabrata<br>32<br>$FEPI_{half}$<br>(2.8)* |
|---|---|---|---|---|---|---|
| 2 | <0.06 | 0.125 | 64 | >64 | >64 | >64 |
| 3 | <0.06 | 0.25 | 8 | 16 | 32 | 32 |
| 4 | 0.125 | 0.25 | 4 | >64 | >64 | >64 |
| 6 | 0.5 | 2 | 2 | 16 | 16 | 16 |
| 7 | 0.5 | 8 | 16 | 16 | >64 | >64 |
| 8 | 0.5 | 2 | 8 | 16 | >64 | >64 |
| 9 | 2 | >64 | 1 | >64 | >64 | >64 |
| 11 | <0.06 | 2 | 4 | >64 | >64 | >64 |
| 15 | 2 | 1 | 4 | >64 | >64 | >64 |
| 16 | 1 | 0.25 | 64 | >64 | >64 | >64 |
| 18 | >64 | >64 | >64 | >64 | >64 | >64 |
| 21 | 1 | 4 | >64 | >64 | >64 | >64 |
| 22 | <0.06 | 1 | 64 | >64 | >64 | >64 |

*$FLU_{half}$ concentrations are shown in parentheses.

As shown in Table 10, most of the milbemycins inhibited efflux pumps of the ABS-family of transporters, originating from C. albicans or C. glabrata. However, none of them showed activity against efflux pumps of the Major Facilitator family. Milbemycins that inhibited individual efflux pumps as well as milbemycins that inhibited multiple efflux pumps were identified.

Example 11

Comparative Potentiation Activity of Various Milbemycins and Related Analogs Against Various Clinical Isolates Potentiation of the activity of azoles by fungal efflux pump inhibitors (FEPIs) was studied in dose-titration assay using a sub-inhibitory concentration of fluconazole and a series of concentrations for the FEPIs. The combinations were tested against a series of Candida strain with known expression of efflux pumps or with complete deletion of all known pumps and Aspergillus fumigatus. Results are reported as minimum inhibitory concentration (MIC) of FEPIs in the presence or absence of FEPIs. A total of 27 distinct milbemycins were studied. Data are summarized in Tables 11 and 12.

The activity of milbemycins in fluconazole potentiation is extremely high against all strains expressing CDR pumps (C. albicans, C. glabrata). Activity was also noted is against C. krusei intrinsically resistant to fluconazole. Milbemycins are clearly FEPIs and there was no significant potentiation of fluconazole against strains lacking efflux pumps (YEM24 and YEM27).

The activity of one milbemycin was also studied in checker-board assays. The MacSynergy 3-D analysis method for drug-drug interaction was used to study the potentiation of two antifungal agents (fluconazole and terbinafine) by FEPIs. It provides information on the extent of synergism between the two drugs and the concentrations at which synergism can be detected. Using differential surface analysis, pick of synergy volumes are quantified for each combination of drugs and strain tested in a traditional checkerboard assay (Table 13).

Finally, the activity of a combination of fluconazole and milbemycin $α_9$ was compared to that of fluconazole alone against 50 clinical isolates of Candida. In C. albicans (n=33) and in C. glabrata (n=12), fluconazole $MIC_{90}$ were reduced by >512-fold and 16-fold respectively (Table 14). Potentiation of fluconazole was also observed in C. lipolytica, C. tropicalis, C. krusei and Cryptococcus neoformans (Table 15). In summary, FEPIs were found to enhance the activity of fluconazole against all yeast clinical isolates hence their potential useful in the management of fungal infections.

TABLE 12

Determination of FEPI MICs for Aspergillus fumigatus in Combination with 1/4 the Azole's MIC at 48 hrs

| 1/4 MIC | FEPI | Fluconazole 32 µg/ml | | Itraconazole 0.063 µg/ml | | Ketoconazole 4 µg/ml | |
|---|---|---|---|---|---|---|---|
| Comp | MIC^ | 80% Inh^ | 60% Inh | 80% Inh^ | 60% Inh | 80% Inh^ | 60% Inh |
| 1 | >64 | >64 | >64 | >64 | >64 | >64 | >64 |
| 2 | >64 | >64 | 2 | >64 | >64 | 0.5 | 0.5 |
| 3 | >64 | >64 | 2 | 16 | 8 | ≦0.063 | ≦0.063 |
| 4 | >64 | >64 | 1 | >64 | 2 | 0.5 | 0.5 |
| 5 | 64 | 64 | 4 | 32 | 0.5 | ≦0.063 | ≦0.063 |
| 6 | >64 | >64 | 2 | >64 | >64 | 4 | ≦0.063 |
| 7 | >64 | >64 | >64 | >64 | >64 | ≦0.063 | ≦0.063 |
| 8 | >64 | >64 | 1 | 8 | 1 | ≦0.063 | ≦0.063 |
| 9 | >64 | >64 | 64 | >64 | 1 | ≦0.063 | ≦0.063 |
| 10 | >64 | 4 | 0.25 | 8 | 1 | 0.25 | 0.25 |
| 11 | >64 | 0.5 | ≦0.063 | 4 | 1 | 0.125 | 0.125 |
| 12 | >64 | >64 | 16 | >64 | 8 | 1 | 0.125 |
| 13 | >64 | >64 | 32 | >64 | 64 | 0.5 | 0.5 |
| 14 | >64 | >64 | 64 | >64 | >64 | 16 | 2 |
| 15 | >64 | >64 | 0.25 | >64 | 1 | 0.25 | 0.25 |

TABLE 12-continued

Determination of FEPI MICs for *Aspergillus fumigatus* in Combination with 1/4 the Azole's MIC at 48 hrs

| 1/4 MIC Comp | FEPI MIC ^ | Fluconazole 32 μg/ml 80% Inh ^ | 60% Inh | Itraconazole 0.063 μg/ml 80% Inh ^ | 60% Inh | Ketoconazole 4 μg/ml 80% Inh ^ | 60% Inh |
|---|---|---|---|---|---|---|---|
| 16 | >64 | >64 | >64 | >64 | 1 | 0.125 | 0.125 |
| 17 | >64 | 64 | 64 | >64 | 16 | 4 | 4 |
| 18 | >64 | >64 | 8 | >64 | >64 | 0.125 | 0.125 |
| 19 | 64 | 64 | 32 | >64 | 8 | ≦0.063 | ≦0.063 |
| 20 | 64 | 4 | 2 | 8 | 0.25 | ≦0.063 | ≦0.063 |
| 21 | >64 | 8 | 8 | 8 | 1 | ≦0.063 | ≦0.063 |
| 22 | >64 | >64 | >64 | >64 | >64 | ≦0.063 | ≦0.063 |
| 23 | >64 | >64 | >64 | >64 | 64 | 8 | ≦0.063 |
| 24 | 64 | 64 | 64 | 64 | 64 | ≦0.063 | ≦0.063 |
| 25 | >64 | 2 | 1 | >64 | 0.5 | 0.25 | ≦0.063 |

^Endpoint determination using NCCLS Criteria for Azoles
MIC Determined as 80% inhibition relative to the growth control
*Aspergillus fumigatus* incubated at 35° C. for 42 hrs in CM Broth

TABLE 13

Synergy Volume Analysis of Potentiation of Fluconazole and Terbinafine

| | Synergy Volume | |
|---|---|---|
| Strain | Fluconazole | Terbinafine |
| *C. albicans*, wt | nd | 2790 |
| *C.albicans* BEN up | 196 | 500 |
| *C. albicans*, CDR1, CDR2, up | 2337 | 1386 |
| *C. albicans* ΔCDR1 ΔCDR2 ΔBEN ΔFLU1 | 0.08 | 169 |
| *C. glabrata*, wt | nd | 478 |
| *C. glabrata*, CgCDR up | 1815 | 392 |
| *C. krusei* | 1178 | 1517 |

TABLE 14

Effect of Milbemycin $\alpha_9$ on Fluconazole Susceptibility in *C. albicans* & *C. glabrata*

| | Fluconazole MIC (μg/ml)* | | | |
|---|---|---|---|---|
| | *C. albicans* (n = 33) | | *C. glabrata* (n = 12) | |
| | Alone | + Milbemycin $\alpha_9$ | Alone | + Milbemycin $\alpha_9$ |
| Range | <0.25–>128 | <0.25–1 | <0.25–>128 | <0.25–16 |
| MIC$_{50}$ | 1 | <0.25 | 32 | 2 |
| MIC$_{90}$ | >128 | <0.25 | >128 | 8 |

*Broth Microdilution MIC (80%) in YPD

TABLE 15

Effect of Milbemycin $\alpha_9$ on Fluconazole Susceptibility in Other Candida species

| | | Fluconazole MIC (μg/ml)* | |
|---|---|---|---|
| Species | Strain | Alone | + Milbemycin $\alpha_9$ |
| *C. lipolytica* | 828B | 128 | 8 |
| *C. tropicalis* | 790C | >128 | ≦0.25 |
| *C. tropicalis* | 794A | >128 | ≦0.25 |
| *C. tropicalis* | 822B | >128 | ≦0.25 |
| *C. neoformans* | 790B | >128 | ≦0.25 |
| *C. krusei* | 94-2696 | 128 | 16 |
| *C. krusei* | 94-2501 | 128 | 16 |

*Broth Microdilution MIC (80%) in YPD

TABLE 11

Determination of FEPI MICs in Combination with 1/8 Fluconazole MIC at 24 hrs.
MIC of Compounds (COMP) in the absence or presence of fluconazole (FLU)[a]

| FLU MIC[b] | YEM 13 *C. albicans* BEN up 64 μg/ml | | YEM 15 *C. albicans*, CDR1CDR2 up 64 μg/ml | | YEM 53 *C. krusei* 64 μg/ml | | YEM 17 *C. glabrata*, CgCDR up 64 μg/ml | | YEM 51 *C. glabrata* wt 64 μg/ml | | YEM 30 *C. albicans* wt 0.5/64 μg/ml[c] | | YEM 24 *C. albicans* ΔCDR1, ΔCDR2 0.25 μg/ml | | YEM 27 *C. albicans* ΔCDR1ΔCDR2 ΔBENΔFLU1 ≦0.125 μg/ml | |
|---|---|---|---|---|---|---|---|---|---|---|---|---|---|---|---|---|
| COMP | − | + | − | + | − | + | − | + | − | + | − | + | − | + | − | + |
| 1 | >64 | >64 | >64 | >64 | >64 | 8 | >64 | >64 | >64 | 64 | >64 | ≦0.03 | >64 | >64 | >64 | 64 |
| 2 | >64 | >64 | >64 | ≦0.03 | >64 | 2 | >64 | 4 | >64 | 16 | >64 | ≦0.03 | >64 | >64 | >64 | 64 |

TABLE 11-continued

Determination of FEPI MICs in Combination with 1/8 Fluconazole MIC at 24 hrs.
MIC of Compounds (COMP) in the absence or presence of fluconazole (FLU)[a]

| FLU MIC[b] | YEM 13 C. albicans BEN up 64 μg/ml | | YEM 15 C. albicans, CDR1CDR2 up 64 μg/ml | | YEM 53 C. krusei 64 μg/ml | | YEM 17 C. glabrata, CgCDR up 64 μg/ml | | YEM 51 C. glabrata wt 64 μg/ml | | YEM 30 C. albicans wt 0.5/64 μg/ml[c] | | YEM 24 C. albicans ΔCDR1, ΔCDR2 0.25 μg/ml | | YEM 27 C. albicans ΔCDR1ΔCDR2 ΔBENΔFLU1 ≦0.125 μg/ml | |
|---|---|---|---|---|---|---|---|---|---|---|---|---|---|---|---|---|
| COMP | − | + | − | + | − | + | − | + | − | + | − | + | − | + | − | + |
| 3 | >64 | 32 | >64 | ≦0.03 | >64 | 0.06 | >64 | 4 | >64 | 16 | >64 | ≦0.03 | >64 | >64 | 8 | 8 |
| 4 | >64 | >64 | >64 | ≦0.03 | >64 | 8 | >64 | 2 | >64 | 4 | >64 | ≦0.03 | >64 | >64 | >64 | 64 |
| 5 | >64 | 64 | >64 | ≦0.03 | >64 | >64 | >64 | 0.125 | >64 | 0.25 | >64 | ≦0.03 | >64 | >64 | >64 | 64 |
| 6 | >64 | >64 | >64 | ≦0.03 | >64 | 8 | >64 | 1 | >64 | 8 | >64 | ≦0.03 | >64 | >64 | >64 | 64 |
| 7 | >64 | >64 | >64 | 0.125 | >64 | 16 | >64 | >64 | >64 | >64 | >64 | ≦0.03 | >64 | >64 | >64 | >64 |
| 8 | >64 | >64 | >64 | 0.125 | >64 | 32 | >64 | 2 | >64 | 8 | >64 | ≦0.03 | >64 | >64 | >64 | >64 |
| 9 | >64 | >64 | >64 | 0.125 | >64 | >64 | >64 | 0.5 | >64 | 1 | >64 | ≦0.03 | >64 | >64 | >64 | >64 |
| 10 | >64 | >64 | >64 | ≦0.03 | >64 | >64 | >64 | 1 | >64 | 2 | >64 | ≦0.03 | >64 | >64 | >64 | >64 |
| 11 | >64 | >64 | >64 | ≦0.03 | >64 | ≦0.03 | >64 | 0.5 | >64 | 1 | >64 | ≦0.03 | >64 | >64 | >64 | >64 |
| 12 | >64 | >64 | >64 | ≦0.03 | >64 | 8 | >64 | 32 | >64 | 8 | >64 | 4 | >64 | >64 | >64 | 64 |
| 13 | >64 | 64 | >64 | 8 | >64 | >64 | >64 | 64 | >64 | >64 | >64 | 0.125 | >64 | >64 | >64 | >64 |
| 14 | >64 | >64 | >64 | 2 | >64 | >64 | >64 | 16 | >64 | 16 | >64 | 4 | >64 | >64 | >64 | >64 |
| 15 | >64 | >64 | >64 | 0.5 | >64 | >64 | >64 | 2 | >64 | 4 | >64 | ≦0.03 | >64 | >64 | >64 | >64 |
| 16 | >64 | 64 | >64 | 0.125 | >64 | >64 | >64 | 32 | >64 | 2 | >64 | ≦0.03 | >64 | >64 | >64 | >64 |
| 17 | >64 | >64 | >64 | ≦0.03 | >64 | >64 | >64 | 2 | >64 | 0.5 | >64 | ≦0.03 | >64 | >64 | >64 | 64 |
| 18 | >64 | >64 | >64 | >64 | >64 | >64 | >64 | >64 | >64 | >64 | >64 | ≦0.03 | >64 | >64 | >64 | >64 |
| 19 | >64 | 16 | >64 | ≦0.03 | >64 | 8 | >64 | 64 | >64 | >64 | 8 | ≦0.03 | >64 | 32 | >64 | 16 |
| 20 | >64 | 64 | >64 | ≦0.03 | >64 | 4 | >64 | 4 | >64 | 2 | >64 | ≦0.06 | >64 | >64 | >64 | 64 |
| 21 | >64 | >64 | >64 | 1 | >64 | 8 | >64 | 8 | >64 | 8 | >64 | 0.125 | >64 | >64 | >64 | >64 |
| 22 | >64 | >64 | >64 | ≦0.03 | >64 | 8 | >64 | >64 | >64 | >64 | >64 | ≦0.03 | >64 | >64 | >64 | >64 |
| 23 | >64 | >64 | >64 | 64 | >64 | >64 | >64 | >64 | >64 | >64 | >64 | ≦0.03 | >64 | >64 | >64 | >64 |
| 24 | >64 | 64 | >64 | ≦0.03 | >64 | >64 | >64 | 1 | >64 | 0.125 | >64 | ≦0.03 | >64 | >64 | >64 | 64 |
| 25 | >64 | >64 | >64 | ≦0.03 | >64 | 0.06 | >64 | 2 | >64 | 4 | >64 | ≦0.03 | >64 | >64 | >64 | >64 |

[a]Compound MIC was determined in the absence or presence of 1/8 × MIC of fluconazole. MIC Determined as 80% inhibition relative to the growth control
[b]Endpoint determination using NCCLS Criteria for Azoles.
[c]For YEM 30, MIC at 24 hours read at 0.5 μg/ml and at 40 hrs increased to 64 μg/ml These results clearly support that FEPIs such as milbemycins potentiate multiple classes of antifungal agents and act through the inhibition of efflux pumps. For example, both milbemycin $\beta_1$ and milbemycin oxime are effective in potentiating the activity of fluconazole against C. albicans which overexpresses the ABC transporter family of pumps (CDR1 and CDR2) and a wild type C. krusei. Milbemycin $\beta_1$ is effective in potentiating the activity of fluconazole against C. glabrata, while milbemycin oxime is not. Neither milbemycin $\beta_1$ nor milbemycin oxime are effective in potentiating the activity of fluconzaole against the C. albicans strain carrying the BEN pump (major facilitator pump family).

While the above description describes particular embodiments and examples illustrating the invention, those skilled in the art will recognize that the invention may be practiced in a variety of alternative ways, for example, using a variety of other milbemycins, milbemycin-type compounds and antimicrobial and anticancer agents, all within the scope of this invention.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The strains, active compounds, and the methods described herein as presently representative of preferred embodiments are exemplary and are not intended as limitations on the scope of the invention. Changes therein and other uses will occur to those skilled in the art, which are encompassed within the spirit of the invention, are defined by the scope of the claims. For example, those skilled in the art will recognize that the identification of additional compounds active on the specified efflux pumps can be carried out as described or in other screening methods using other techniques, and can be performed using any of a large number of different strains or species of microbes or cells.

It will be readily apparent to one skilled in the art that varying substitutions and modifications may be made to the invention disclosed herein without departing from the scope and spirit of the invention. For example, using other strains and cells and antimicrobial agents are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims

What we claim is:

1. A method for inhibiting the growth of a fungal cell known or suspected to have an efflux pump resistance mechanism to an antifungal compound, comprising contacting the cell with a milbemycin compound or derivative thereof and the antifungal compound whereby the milbemycin compound or derivative thereof inhibits the efflux pump and enhances the susceptibility of the fungal cell to the antifungal compound.

2. The method of claim 1, wherein said fungal cell is a Candida species selected from the group consisting of *C. albicans, C. krusei* and *C. Glabrata.*

3. The method of claim 1, wherein said milbemycin compound or derivative thereof comprises Structure I:

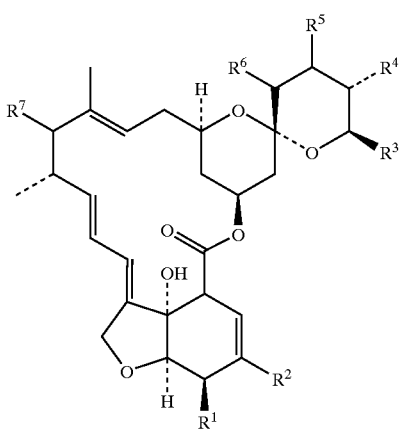

(I)

wherein independently $R^1$=O, OH, or $OCH_3$;

$R^2$=$CH_3$, $CH_2OCOCH_2CH_2CH_3$, $CH_2OCOCH(CH_3)_2$, $CH_2OCOCH_2CH_2CH_2CH_3$, $CH_2OCOCH_2CH(CH_3)_2$, $CH_2OCOCH_2CH(CH_3)CH_2CH_3$, $CH_2OCOCH_2CH(CH_2CH_3)_2$, $CH_2OCOCH=CHCH_3$, $CH_2OCOCH=C(CH_3)_2$, $CH_2OCOCH=C(CH_3)(CH_2CH_3)$, $CH_2OCOCH=C(CH_2CH_3)_2$, $CH_2OCOC(CH_3)=CHCH_3$, or

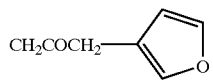

$R^3$=$CH_3$, $CH_2CH_3$, $CH(CH_3)_2$, $CH_2C(CH_3)CH_2CH_3$, $C(CH_3)=CH(CH_3)$, $C(CH_3)=CH(CH_2CH_3)$, $C(CH_3)=CH(CH(CH_3)_2)$, or $C(CH_3)=CH(CH_3)$;

$R^4$=$CH_3$, or $CH_2CH_3$;

$R^5$=H, OH, $OCOCH(CH_3)_2$, $OCOCH(CH_3)Bu^n$, $OCOC_4H_9$; or $OCOC_6H_{13}$;

$R^6$=H, or OH; and $R^7$=H, OH, $OCOCH(CH_3)_2$, or $OCOCH_2CH(CH_3)_2$.

4. The method of claim 1, wherein said milbemycin compound or derivative thereof comprises Structure II:

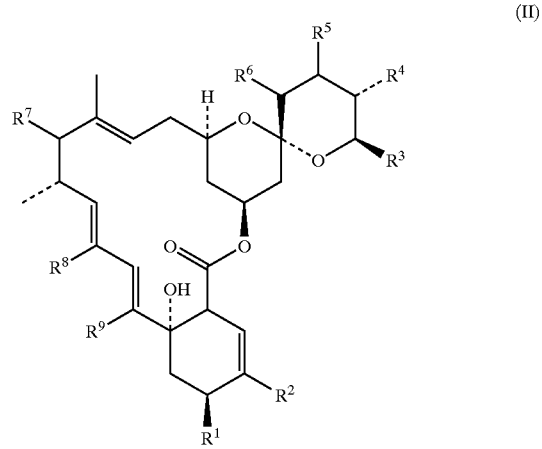

(II)

wherein independently $R^1$=O, OH, or $OCH_3$;

$R^2$=$CH_3$, $CH_2OCOCH_2CH_2CH_3$, $CH_2OCOCH(CH_3)_2$, $CH_2OCOCH_2CH_2CH_2CH_3$, $CH_2OCOCH_2CH(CH_3)_2$, $CH_2OCOCH_2CH(CH_3)CH_2CH_3$, $CH_2OCOCH_2CH(CH_2CH_3)_2$, $CH_2OCOCH=CHCH_3$, $CH_2OCOCH=C(CH_3)_2$, $CH_2OCOCH=C(CH_3)(CH_2CH_3)$, $CH_2OCOCH=C(CH_2CH_3)_2$, $CH_2OCOC(CH_3)=CHCH_3$, $CH_2O_2CCH_2C_6H_5$, or

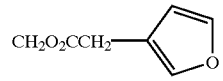

$R^3$=$CH_3$, $CH_2CH_3$, $CH(CH_3)_2$, $CH_2C(CH_3)CH_2CH_3C(CH_3)=CH(CH_3)$, $C(CH_3)=CH(CH_2CH_3)$, $C(CH_3)=CH(CH(CH_3)_2)$, or $C(CH_3)=CH(CH_3)$;

$R^4$=$CH_3$, or $CH_2CH_3$;

$R^5$=H, OH, $OCOCH(CH_3)_2$, $OCOCH(CH_3)Bu^n$, $OCOC_4H_9$; or $OCOC_6H_{13}$;

$R^6$=H, or OH;

$R^7$=H, OH, $OCOCH(CH_3)_2$, or $OCOCH_2CH(CH_3)_2$;

$R^8$=$CH_3$, $CH_2OH$, or CHO; and $R^9$=H, or OH.

5. The method of claim 1, wherein said milbemycin compound or derivative thereof comprises Structure III:

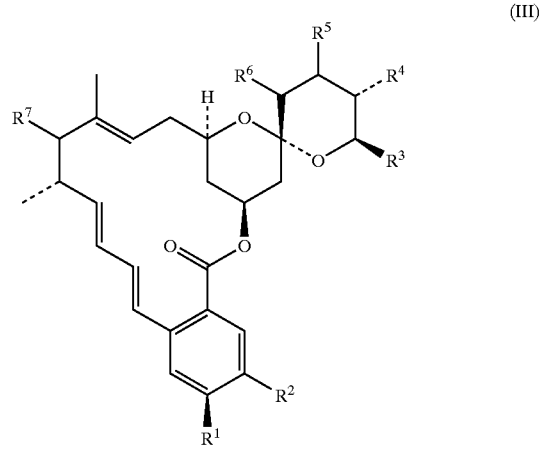

(III)

wherein independently $R^1$=OH;

$R^2$=$CH_3$, $CH_2OCOCH_2CH_2CH_3$, $CH_2OCOCH(CH_3)_2$, $CH_2OCOCH_2CH_2CH_3$, $CH_2OCOCH_2CH(CH_3)_2$, $CH_2OCOCH_2CH(CH_3)CH_2CH_3$, $CH_2OCOCH_2CH(CH_2CH_3)_2$, $CH_2OCOCH=CHCH_3$, $CH_2OCOCH=C(CH_3)_2$, $CH_2OCOCH=C(CH_3)(CH_2CH_3)$, $CH_2OCOCH=C(CH_2CH_3)_2$, $CH_2OCOC(CH_3)=CHCH_3$, $CH_2O_2CCH_2C_6H_5$, or

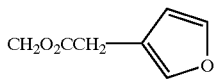

$R^3 = CH_3$, $CH_2CH_3$, $CH(CH_3)_2$, $CH_2C(CH_3)CH_2CH_3$, $C(CH_3)=CH(CH_3)$, $C(CH_3)=CH(CH_2CH_3)$, $C(CH_3)=CH(CH(CH_3)_2)$, or $C(CH_3)=CH(CH_3)$;

$R^4 = CH_3$, or $CH_2CH_3$;

$R^5 = H$, $OH$, $OCOCH(CH_3)_2$, $OCOCH(CH_3)Bu^n$, $OCOC_4H_9$; or $OCOC_6H_{13}$;

$R^6 = H$, or $OH$; and $R^7 = H$, $OH$, $OCOCH(CH_3)_2$, or $OCOCH_2CH(CH_3)_2$.

6. The method of claim 1, wherein said milbemycin compound or derivative thereof is selected from the group consisting of a B-41 compound or a derivative thereof, an S-541 compound or a derivative thereof, an LL-F28249 compound or a derivative thereof, an N 787-182 compound or a derivative thereof, and a VM series compound or a derivative thereof.

7. The method of claim 1, wherein said fungal cell is in contact with said milbemycin compound or derivative thereof and said antifungal compound simultaneously.

8. The method of claim 1, wherein said fungal cell is first contacted with said milbemycin compound or derivative thereof and then is contacted with said antifungal compound.

9. The method of claim 1, wherein said fungal cell is resistant to said antifungal compound.

10. The method of claim 1, wherein said milbemycin compound is a milbemycin derivative.

11. The method of claim 1, wherein said milbemycin compound or derivative thereof is prepared by chemical modification of a natural mylbemycin compound.

12. The method of claim 1, wherein said milbemycin compound or derivative thereof is active on a CDR1, CDR2, BEN or FLU1 efflux pump or a homolog thereof.

* * * * *